(12) United States Patent
Finkelmeier et al.

(10) Patent No.: US 11,887,708 B2
(45) Date of Patent: *Jan. 30, 2024

(54) END OF SERVICE SUMMARY REPORT FOR MOBILE CARDIAC OUTPATIENT TELEMETRY

(71) Applicant: Braemar Manufacturing, LLC, Eagan, MN (US)

(72) Inventors: Jeffrey R. Finkelmeier, Collegeville, PA (US); Wayne Michael Derkac, Walloon Lake, MI (US)

(73) Assignee: Koninklijke Philips N.V., Eindhoven (NL)

( * ) Notice: Subject to any disclaimer, the term of this patent is extended or adjusted under 35 U.S.C. 154(b) by 41 days.

This patent is subject to a terminal disclaimer.

(21) Appl. No.: 17/223,563

(22) Filed: Apr. 6, 2021

(65) Prior Publication Data

US 2021/0280283 A1    Sep. 9, 2021

Related U.S. Application Data

(63) Continuation of application No. 15/678,594, filed on Aug. 16, 2017, now Pat. No. 11,017,887.
(Continued)

(51) Int. Cl.
| | | |
|---|---|---|
| *G16H 10/60* | (2018.01) | |
| *A61B 5/361* | (2021.01) | |
| (Continued) | | |

(52) U.S. Cl.
CPC .......... *G16H 10/60* (2018.01); *A61B 5/0245* (2013.01); *A61B 5/346* (2021.01); *A61B 5/361* (2021.01); *A61B 5/363* (2021.01); *G16H 15/00* (2018.01)

(58) Field of Classification Search
CPC ...... G16H 10/60; G16H 15/00; A61B 5/0245; A61B 5/04012; A61B 5/046; A61B 5/0464; G06F 19/3418
See application file for complete search history.

(56) References Cited

U.S. PATENT DOCUMENTS

| | | | | |
|---|---|---|---|---|
| 5,099,424 A | * | 3/1992 | Schneiderman | G16H 10/60 |
| | | | | 705/3 |
| 2010/0268103 A1 | * | 10/2010 | McNamara | A61B 5/361 |
| | | | | 600/523 |

FOREIGN PATENT DOCUMENTS

CN    102697492 B  *  8/2014

OTHER PUBLICATIONS

"St. Jude Medical Announces Agreement With Lumedx to Manage Cardiovascular Patient Data." Business Wire. Jul. 6, 2006: NA. (Year: 2006).*

* cited by examiner

Primary Examiner — Linh Giang Le

(57) ABSTRACT

A method for filtering ECG data includes receiving ECG data of a patient, generating an ECG report comprising a plurality of pages, and presenting priority information on a first page of the plurality of pages. The priority information includes information identifying the patient, monitoring summary information including an indication of a total duration of a monitoring period, heart rate summary information including an average heart rate, a fastest heart rate, and a slowest heart rate, representative arrhythmia summary information including a count of ECG strips containing each of a plurality of types of cardiac arrhythmia, and atrial fibrillation summary information including an indication of atrial fibrillation burden during the monitoring period. The first page of the report does not include an ECG strip.

20 Claims, 43 Drawing Sheets

Related U.S. Application Data

(60) Provisional application No. 62/375,738, filed on Aug. 16, 2016.

(51) Int. Cl.
  *A61B 5/363* (2021.01)
  *A61B 5/346* (2021.01)
  *G16H 15/00* (2018.01)
  *A61B 5/0245* (2006.01)

UNIFIED ARRHYRHMIA  Patient: Example Patient (F),
DIAGNOSTIC SYSTEM   DOB: 2012-Jul-02   ID: 9483829401  3
                    Phone: 817 582 9527

Mobile Cardiac Telemetry - End of Study Report

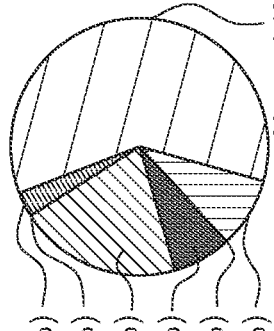

Ordering physician: Physician Ordering
Physician's phone: 800 321 123
Physician's address: 245 West 107th St. Suite 11A
New York, NY 10025
USA Recorded time: 30d 0h 0m (3178069 beats)
Monitoring dates: 2012-Apr-13 to 2012-May-13
Interpreting physician: Interpreting Physician
Referring physician: not set
Reason: 785.0 Racing Heart, 780.4 Dizziness, 785.1 Palpitations VE (3.15%)
SVE (0.19%)
Afib / AFL (20.10%)
Bradycardia (7.34%)
Pause / Block (0.00%)
Nondiagnostic (9.05%)
Normal (60.16%)

Arrhythmia Summary

Patient Triggered         18 events total    Patient Triggered: Racing Heart during Afib / AFL at 12:44:25 d23
With symptoms             18 events
Correlated with arrhythmias  18 events
Most frequent (15 events) Racing Heart | Afib / AFL → [page 11]
Second frequent (3 events) Dizziness | Bradycardia Atrial Fibrillation / Flutter  20.10 %           Fastest Afib / AFL minutely rate: 173 BPM at 10:51:29 d9
Fastest minutely rate     170 BPM at 10:51 d9 → [page 10]
Average minutely rate     99 BPM
Slowest minutely rate     64 BPM at 08:17 d23
Longest episode           42h 39m 28s at 23:00 d25

ECG Strips

| | | |
|---|---|---|
| Sinus Rhythm | 67.50 % | Fastest Sinus minutely rate: 128 BPM at 17:34:45 d24 |
| Fastest minutely rate | 128 BPM at 17:34 d24 → page 12 | |
| Average minutely rate | 70 BPM | |
| Slowest minutely rate | 49 BPM at 04:05 d3 | |
| Bradycardia | 7.34 % | |
| Pause & Block | - | Slowest Bradycardia N-N: 1590 ms (38 BPM) at 01:50:57 d2 |
| Missed Beat | - | |
| Pause (>2 s) | - | |
| Asystole (>3.5 s) | - | |
| Slowest Bradycardia N-N | 38 BPM at 01:50 d2 → page 09 | |
| Ventricular | 3.15 % | Fastest Ventricular Triplet: 183 BPM at 20:26:43 d3 |
| Single | Couplet | Triplet | 61691 | 480 | 5 events → page 09 | |
| Runs (>3 beats) | - | |
| Longest run | - | |
| Fastest run | - | |
| Supraventricular | 0.19 % | Fastest Supraventricular Run: 163 BPM at 16:37:32 d5 |
| Single | Couplet | Triplet | 5135 | 1329 | 66 events | |
| Runs (>3 beats) | 47 episodes | |
| Longest run | 12 beats at 11:44 d15 | |
| Fastest run | 163 BPM at 16:37 d5 → page 10 | |

Diagnostic findings: Sinus rhytm with intermittent atrial fibrillation. Frequent PVCs and occasional PACs. PAC runs noted also.

Physician Interpretation:

FIG. 4B

Example #1, Patch Report

| Date of Birth | Gender | Patient ID | Primary Indication | Enrollment Period | Analysis Time |
|---|---|---|---|---|---|
| 01/01/37 (74 yrs) | Male | 1234-5678 | Atrial fibrillation | 6 days 19 hours<br>11/16/10, 10:22 am to<br>11/23/10, 05:51am | 6 days 18 hours<br>(after artifact removed) |

Prescribing Physician: Clinic
Example Physician: Paradiso

Ventricular Tachycardia (4 beats or more)

▼ Fastest VT (118 bpm)  No. of Episodes: 1

Patient Triggered Event? (± 45s)  YES ☐  NO ☒

Heart Rate
Maximum HR  171 bpm (at 03:15pm on 11/19)
Minimum HR  8 bpm (at 05:59am on 11/17)
Average HR  63 bpm

Supraventricular Tachycardia (4 beats or more)

▼ Fastest SVT (171 bpm)  No. of Episodes: 6

YES ☐  NO ☒

Patient Triggered Events
Number of Triggered Events: 18
Findings within ± 45 sec of trigger:
Atrial Fibrillation
Supraventricular Ectopic beat(s)
Sinus Rhythm (E)

FIG. 5A

Pauses (3 secs or longer)
▼Longest Pause (7.8 secs, 8 bpm)   No. of Episodes: 58

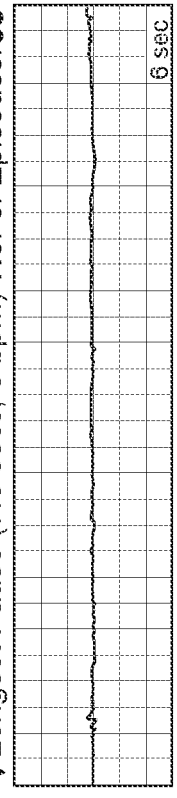

YES ☐  NO ☒

Atrial Fibrillation
▼Fastest Fibrillation (149 bpm)   AF Burden: 29%

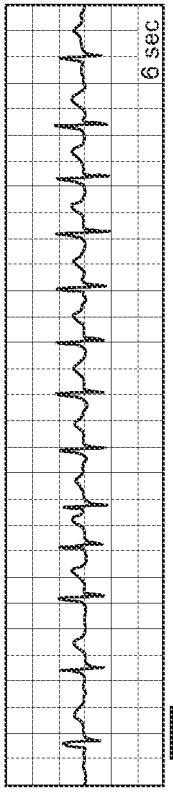

YES ☐  NO ☒

AV Block (2nd° Mobitz II, 3rd°)

None found

Ⓔ

Ectopics

Supraventricular Ectopic Counts
Isolated   5662   0.9%   Rare
Couplet     87   <0.1%  Rare
Triplet      8   <0.1%  Rare Ventricular Ectopic Beats (VE/PVCs)
Isolated    13    0.1%   Rare
Couplet      1   <0.1%  Rare
Triplet      0

Ventricular Trigeminy    0.0 secs
Ventricular Bigeminy     0.0 secs

Physician Comments

_____
SIGNATURE

Findings
Patient had a min HR of 33 bpm, max HR of 171 bpm, and avg HR of 62 bpm. Predominant underlying rhytm was Sinus Rhythm. 1 run of Ventricular Tachycardia occured lasting 6 beats with a max rate of 118 bpm. 6 Supraventricular Tachycardia runs occured, the fastest run lasting 4 beats with a max rate of 171 bpm (avg of 80 bpm). Atrial Fibrillation occured (29% burden), ranging from 39-149 bpm (avg of 80 bpm). Atrial Fibrillation was detected within ±45 seconds of the patient pressing the trigger button. 58 Pause(s) occured, the longest 7.8 secs. SVEs (eg PACs) were present. VEs (eg PVCs) were present. MD notification criteria for Pauses met - notified Dr. Physician on 12/01/2010 at 12:00 PM CST (Tech AA).

FIG. 5B

Mobile Cardiac Outpatient Telemetry (MCOT)

(Tel) 866-426-4401 (Fax) 866-426-4403

End of Service Summary Report      8/9/2016

Patient Name: Irina Navasartyan      Notification Physician: Peter M. Doe, MD
Date of Birth: 12/12/1999 (age 16)      San Diego Cardiac Center
Gender: F      3550 Alta Firam Drive app#3456667879
Patient Phone: (223)234-2344      San Deigo, CA 92100
Medical Record:      Ordering Physician: Charles A. Doe, MD
Diagnosis(ICD9): 340 Multiple sclerosis      Referring Physician: Dr. Shinder Frank

Monitoring Summary
- Time Monitered: 12d 12h 5m
- Prescription Days: 50
- Days Monitored: 17
- Baseline Date: 07/19/16
- End Date: 06/09/16

Event Summary
- Total Strip Count: 64
- Symotomatic: 19
- Asymptomatic: 45
- Emergent/Urgent Count: 4
- Strips on page 8

HR Summary
- High HR: 225 bpm at 07/21/2016 10:49 PDT
- Low HR: 30 bpm at 07/18/2016 17:16 PDT
- Avg HR: 93 bpm
- Daily HR and High/Low strips on page 3

FIG. 6A

| Representative Arrhythmia Summary | Strips located on page 8 | | | Total Strip Count (TSC) |
|---|---|---|---|---|
| AF (Fastest) | Sx 07/28/2016 11:06 PDT | HR: 211 | Sx: Heart Racing, Short of Breath, Skipped Beat | TSC: 5 |
| | ASx 07/25/2016 18:17 PDT | HR: 201 | ASx: Auto Trigger | TSC: 10 |
| SVT (Fastest) | Sx 08/02/2016 10:50 PDT | HR: 222 | Sx: Symptom other than listed _110_ | TSC: 4 |
| | ASx 08/04/2016 00:59 PDT | HR: 212 | ASx: Auto Trigger | TSC: 4 |
| Pause (Longest) | Sx 07/28/2016 11:00 PDT | L: 12.0s | Sx: Chest Pain, Heart Racing, Short of Breath | TSC: 2 |
| | ASx 07/24/2016 12:30 PDT | L: 13.0s | ASx: Auto Trigger | TSC: 6 |
| Heart Block (Slowest) | 1° 08/02/2016 10:50 PDT | HR: 11 | Sx: Symptom other than listed | TSC: 6 |
| | 2° 07/28/2016 10:59 PDT | HR: 11 | Sx: Chest Pain, Heart Racing, Short of Breath | TSC: 7 |
| | 3° 08/02/2016 10:50 PDT | HR: 11 | Sx: Symptom other than listed | TSC: 1 |
| | AVB 08/02/2016 10:50 PDT | HR: 11 | Sx: Symptom other than listed | TSC: 9 |
| SVT (Fastest) | Sx 07/25/2016 17:26 PDT | HR: 210 | Sx: Heart Racing, Symptom other than listed | TSC: 3 |
| | ASx 08/04/2016 00:59 PDT | HR: 203 | ASx: Auto Trigger | TSC: 10 |

AF Summary | Daily AF Burden/ Duration on page 2

| | | | IN AF | NOT IN AF |
|---|---|---|---|---|
| AF Burden: | 22% | High HR: | 200 bpm \| 07/19/2016 13:46 PDT | 225 bpm \| 07/21/2016 10:49 PDT |
| Analysis Time: | 12d 10h 36m | Low HR: | 30 bpm \| 07/18/2016 17:16 PDT | 30 bpm \| 07/18/2016 17:18 PDT |
| Total Time in AF: | 66h 4m | Avg HR: | 66 bpm | 101 bpm |
| # AF Episodes: | 8 | | | |
| Longest AF: | 1d 0h 0m | | | |

Physician Comments

_____
Signature                Date

FIG. 6B (a) AF is present but due to episodes of < 30 seconds in duration and/or presence of significant artifact, AF burden cannot be accurately calculated.

Emergent/Urgent Summary

| Date | Symptoms | Findings | HR |
|---|---|---|---|
| 07/18/2016 17:10:37 PDT | None Indicated | test | 35 |
| 07/18/2016 17:10:37 PDT | None Indicated | Not correct findings | 11 |
| 07/18/2016 17:10:38 PDT | None Indicated | mine | 11 |
| 07/18/2016 17:10:40 PDT | None Indicated | 2nd degree Heart Block | 11 |
| 07/18/2016 17:10:42 PDT | None Indicated | test | 29 |
| 07/18/2016 17:10:44 PDT | None Indicated | Sinus Rhythm OR Sinus Bradycardia with 1st degree heart block | 35 |
| 07/18/2016 17:10:48 PDT | None Indicated | 1st Degree AVB | 11 |
| 07/18/2016 17:48:40 PDT | Auto Trigger | 1st Degree AVB | 20 |
| 07/18/2016 23:08:35 PDT | Auto Trigger | Ventricular Tachycardia | 69 |
| 07/18/2016 23:08:39 PDT | Auto Trigger | Ventricular Tachycardia | 130 |
| 07/18/2016 23:19:37 PDT | Auto Trigger | Advanced Heart Block | 60 |

FIG. 9B

Emergent/Urgent Summary — 404

| Date | Symptoms | Findings | HR |
|---|---|---|---|
| 07/18/2016 23:19:41 PDT | Auto Trigger | h Advanced Heart Block | 81 |
| 07/18/2016 23:30:39 PDT | Auto Trigger | 8 Second Pause | 30 |
| 07/18/2016 23:30:42 PDT | Auto Trigger | Pauses | 30 |
| 07/18/2016 23:30:43 PDT | Auto Trigger | 9 Second Pause | 20 |
| 07/18/2016 23:41:41 PDT | Auto Trigger | Supraventricular Tachycardia | 30 |
| 07/18/2016 23:41:41 PDT | Auto Trigger | PIE | 30 |
| 07/18/2016 23:52:43 PDT | Auto Trigger | Atrial Fibrillation | 30 |
| 07/19/2016 12:20:00 PDT | Auto Trigger | adh Urgent-representing | 30 |
| 07/19/2016 12:20:02 PDT | Auto Trigger | adh Advanced Heart Block | 30 |
| 07/19/2016 12:20:05 PDT | Auto Trigger | Advanced Heart Block | 78 |
| 07/19/2016 13:18:04 PDT | Auto Trigger | Ventricular Tachycardia | 156 |
| 07/19/2016 13:38:32 PDT | Auto Trigger | Atrial Fibrillation | 136 |
| 07/19/2016 16:59:51 PDT | Auto Trigger | 1st Degree AVB | 20 |
| 07/20/2016 01:17:29 PDT | Auto Trigger | PIE | 160 |
| 07/20/2016 04:59:11 PDT | Auto Trigger | Advanced Heart Block | 40 |

FIG. 10A

| | | | |
|---|---|---|---|
| 07/20/2016 04:59:11 PDT | Auto Trigger | 8 Second Pause | 160 |
| 07/20/2016 04:59:13 PDT | Auto Trigger | PIE | 160 |
| 07/20/2016 04:59:14 PDT | Auto Trigger | Ventricular Tachycardia | 55 |
| 07/20/2016 04:59:17 PDT | Auto Trigger | Atrial Fibrillation | 88 |
| 07/21/2016 10:46:49 PDT | Short of Breath, Symptom other than listed | Advanced Heart Block | 30 |
| 07/21/2016 10:46:52 PDT | Short of Breath, Symptom other than listed | 2nd Degree Heart BlockType 2 | 33 |
| 07/21/2016 15:47:57 PDT | Chest Pain | Atrial Fibrillation | 195 |
| 07/21/2016 15:48:00 PDT | Chest Pain | test represeting | 31 |
| 07/22/2016 14:46:37 PDT | Short of Breath, Symptom other than listed | test | 195 |
| 07/22/2016 14:46:41 PDT | Short of Breath, Symptom other than listed | test | 200 |
| 07/22/2016 17:00:09 PDT | Auto Trigger | test | 220 |
| 07/23/2016 17:00:09 PDT | Auto Trigger | Atrial Fibrillation | 80 |
| 07/24/2016 12:30:02 PDT | Auto Trigger | 13 Second Pause | 66 |
| 07/18/2016 22:02:24 PDT | Auto Trigger | urgent-represeting | 30 |
| 07/19/2016 05:12:39 PDT | Auto Trigger | test | 30 |
| 07/19/2016 06:29:54 PDT | Auto Trigger | Supraventricular Tachycardia | 30 |
| 07/19/2016 16:51:51 PDT | Auto Trigger | 12 Second Pause | 20 |

FIG. 10B

Emergent/Urgent Summary 600 ←  404 ↙

| Date | Symptoms | Findings | HR |
|---|---|---|---|
| 07/22/2016 14:47:19 PDT | Short of Breath, Symptom other than listed | Supraventricular Tachycardia | 100 |
| 07/22/2016 14:47:30 PDT | Short of Breath, Symptom other than listed | Supraventricular Tachycardia | 180 |
| 07/22/2016 16:59:18 PDT | Auto Trigger | Supraventricular Tachycardia | 130 |
| 07/24/2016 12:30:03 PDT | Auto Trigger | 13 Second Pause | 87 |
| 07/25/2016 17:26:40 PDT | Heart Racing, Symptom other than listed | Ventricular Tachycardia | 210 |
| 07/25/2016 18:17:29 PDT | Auto Trigger | Atrial Fibrillation | 199 |
| 07/25/2016 18:17:31 PDT | Auto Trigger | Atrial Fibrillation | 201 |
| 07/26/2016 11:01:02 PDT | Skipped Beat, Light Headed, Short of Breath, Heart Racing, Fainted, Dizzy, Chest Pain, Symptom other than listed | Supraventricular Tachycardia and manyprepoierpoeri poopmzpoxmc-08-08294j23nlkncl cz, x czlkjczicopu09ad-03j-0js-ofja-0ja-djaopdjad-aida-0jopn3*(& | 215 |
| 07/26/2016 15:06:55 PDT | Short of Breath, Chest Pain | Advanced Heart Block | 21 |
| 07/26/2016 15:15:59 PDT | Heart Racing, Fainted | 13 Second Pause | 160 |
| 07/26/2016 15:16:05 PDT | Heart Racing, Fainted | 2nd Degree AVB, Type 1 | 21 |
| 07/26/2016 15:16:11 PDT | Heart Racing, Fainted | test | 19 |

| 07/26/2016 15:49:44 PDT | Skipped Beat, Light Headed, Short of Breath, Heart Racing, Fainted, Dizzy, Chest Pain, Symptom other than listed | 14 Second Pause | 160 |
| 07/26/2016 15:49:47 PDT | Skipped Beat, Light Headed, Short of Breath, Heart Racing, Fainted, Dizzy, Chest Pain, Symptom other than listed | Ventricular Tachycardia | 160 |
| 07/27/2016 16:17:14 PDT | Auto Trigger | Ventricular Tachycardia | 24 |
| 08/05/2016 10:57:07 PDT | Heart Racing, Symptom other than listed | urgent | 151 |

Symptomatic Events Summary

| Date | Symptoms | Findings | HR |
|---|---|---|---|
| 07/21/2016 10:46:49 PDT | Short of Breath, Symptom other than listed | Advanced Heart Block | 30 |
| 07/21/2016 10:46:52 PDT | Short of Breath, Symptom other than listed | 2nd Degree Heart Block Type 2 | 33 |
| 07/21/2016 15:47:57 PDT | Chest Pain | Atrial Fibrillation | 195 |
| 07/21/2016 15:48:00 PDT | Chest Pain | test represeting | 31 |
| 07/22/2016 14:46:37 PDT | Short of Breath, Symptom other than listed | test | 195 |
| 07/22/2016 14:46:41 PDT | Short of Breath, Symptom other than listed | test | 200 |
| 07/22/2016 14:47:19 PDT | Short of Breath, Symptom other than listed | Supraventricular Tachycardia | 100 |

FIG. 11B

Symptomatic Events Summary 700

| Date | Symptoms | Findings | HR |
|---|---|---|---|
| 07/22/2016 14:47:30 PDT | Short of Breath, Symptom other than listed | Supraventricular Tachycardia | 180 |
| 07/25/2016 17:26:40 PDT | Heart Racing, Symptom other than listed | Ventricular Tachycardia | 210 |
| 07/26/2016 11:01:02 PDT | Skipped Beat, Light Headed, Short of Breath, Heart Racing, Fainted, Dizzy, Chest Pain, Symptom other than listed | Supraventricular Tachycardia and manyprepoierpoeri poopmzpoxmc-08-08294j23nlkncl cz, x czlkjczicopu09ad-03j-0js-ofja-0ja-djaopdjad-aida-0jopn3 *(& | 215 |
| 07/26/2016 15:06:55 PDT | Short of Breath, Chest Pain | Advanced Heart Block | 21 |
| 07/26/2016 15:15:59 PDT | Heart Racing, Fainted | 13 Second Pause | 160 |
| 07/26/2016 15:16:05 PDT | Heart Racing, Fainted | 2nd Degree AVB, Type 1 | 21 |
| 07/26/2016 15:16:11 PDT | Heart Racing, Fainted | test | 19 |
| 07/26/2016 15:49:44 PDT | Skipped Beat, Light Headed, Short of Breath, Heart Racing, Fainted, Dizzy, Chest Pain, Symptom other than listed | 14 Second Pause | 160 |
| 07/26/2016 15:49:47 PDT | Skipped Beat, Light Headed, Short of Breath, Heart Racing, Fainted, Dizzy, Chest Pain, Symptom other than listed | Ventricular Tachycardia | 160 |

FIG. 12A

| | | |
|---|---|---|
| 07/28/2016 10:59:31 PDT | Skipped Beat, Light Headed, Short of Breath, Heart Racing, Fainted, Dizzy, Chest Pain, Symptom other than listed | 1st Degree AVB | 13 |
| 07/28/2016 10:59:37 PDT | Skipped Beat, Light Headed, Short of Breath, Heart Racing, Fainted, Dizzy, Chest Pain, Symptom other than listed | Advanced Heart Block | 12 |
| 07/28/2016 10:59:43 PDT | Skipped Beat, Light Headed, Short of Breath, Heart Racing, Fainted, Dizzy, Chest Pain, Symptom other than listed | 2nd Degree AVB | 14 |
| 07/28/2016 10:59:49 PDT | Skipped Beat, Light Headed, Short of Breath, Heart Racing, Fainted, Dizzy, Chest Pain, Symptom other than listed | 2nd Degree AVB, Type 1, Wenckebach | 11 |
| 07/28/2016 10:59:55 PDT | Skipped Beat, Light Headed, Short of Breath, Heart Racing, Fainted, Dizzy, Chest Pain, Symptom other than listed | 2nd Degree AVB, Type 2 | 17 |
| 07/28/2016 11:00:01 PDT | Skipped Beat, Light Headed, Short of Breath, Heart Racing, Fainted, Dizzy, Chest Pain, Symptom other than listed | 2:1 Conduction | 18 |
| 07/28/2016 11:00:07 PDT | Skipped Beat, Light Headed, Short of Breath, Heart Racing, Fainted, Dizzy, Chest Pain, Symptom other than listed | test | 11 |
| 07/28/2016 10:00:13 PDT | Skipped Beat, Light Headed, Short of Breath, Heart Racing, Fainted, Dizzy, Chest Pain, Symptom other than listed | Atrial Bigeminy | 10 |

FIG. 12B

Symptomatic Events Summary

| Date | Symptoms | Findings | HR |
|---|---|---|---|
| 07/28/2016 11:00:19 PDT | Skipped Beat, Light Headed, Short of Breath, Heart Racing, Fainted, Dizzy, Chest Pain, Symptom other than listed | Ventricular Tachycardia | 111 |
| 07/28/2016 11:00:25 PDT | Skipped Beat, Light Headed, Short of Breath, Heart Racing, Fainted, Dizzy, Chest Pain, Symptom other than listed | 12 Second Pause | 140 |
| 07/28/2016 11:00:31 PDT | Skipped Beat, Light Headed, Short of Breath, Heart Racing, Fainted, Dizzy, Chest Pain, Symptom other than listed | Supraventricular Tachycardia | 199 |
| 07/28/2016 11:01:01 PDT | Skipped Beat, Light Headed, Short of Breath, Heart Racing, Fainted, Dizzy, Chest Pain, Symptom other than listed | Advanced Heart Block | 19 |
| 07/28/2016 11:06:34 PDT | Skipped Beat, Light Headed, Short of Breath, Heart Racing, Symptom other than listed | Atrial Fibrillation | 211 |
| 08/02/2016 10:50:01 PDT | Short of Breath, Symptom other than listed | Atrial Fibrillation | 168 |
| 08/02/2016 10:50:09 PDT | Symptom other than listed | 12 Second Pause | 75 |
| 08/02/2016 10:50:13 PDT | Symptom other than listed | Advanced Heart Block | 11 |
| 08/02/2016 10:50:17 PDT | Symptom other than listed | Atrial Fibrillation | 199 |

FIG. 13A

| | | | |
|---|---|---|---|
| 08/02/2016 10:50:18 PDT | Symptom other than listed | Ventricular Tachycardia | 201 |
| 08/02/2016 10:50:28 PDT | Symptom other than listed | Supraventricular Tachycardia | 222 |
| 08/02/2016 10:50:37 PDT | Symptom other than listed | 2nd Degree AVB | 11 |
| 08/02/2016 10:50:51 PDT | Symptom other than listed | 3rd Degree AVB | 11 |
| 08/02/2016 10:50:58 PDT | Symptom other than listed | 1st Degree AVB | 11 |
| 08/03/2016 12:04:21 PDT | Light Headed, Short of Breath, Heart Racing, Chest Pain, | Atrial Fibrillation | 150 |
| 08/05/2016 10:57:07 PDT | Heart Racing, Symptom other than listed | urgent | 151 |

Strip Summary

Date: 07/18/2016 | 17/10/37 PDT
Findings: test
Symptoms: None Indicated
Activities: Baseline Recording
HR: 35

FIG. 13B

Strip Summary

Date: 07/18/2016 | 17:10:37 PDT — 802
Findings: Not correct findings
Symptoms: None Indicated
Activities: Baseline Recording
HR: 11

Date: 07/18/2016 | 17:10:38 PDT
Findings: mine
Symptoms: None Indicated
Activities: Baseline Recording
HR: 11

Date: 07/18/2016 | 17:10:40 PDT
Findings: 2nd degree Heart Block
Symptoms: None Indicated
Activities: Baseline Recording
HR: 11

Date: 07/18/2016 | 17:10:42 PDT
Findings: test
Symptoms: None Indicated
Activities: Baseline Recording
HR: 29

Date: 07/18/2016 | 17:10:44 PDT
Findings: Sinus Rhythm OR Sinus Bradycardia with1st degree heart block
Symptoms: None Indicated
Activities: Baseline Recording
HR: 35

FIG. 14

Strip Summary

Date: 07/18/2016 | 17:10:48 PDT
Findings: 1st Degree AVB
Symptoms: None Indicated
Activities: Baseline Recording
HR: 11

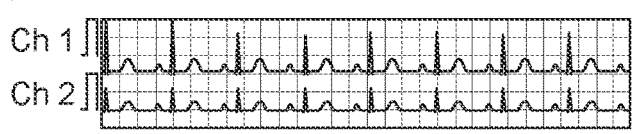

Date: 07/18/2016 | 17:48:40 PDT
Findings: 1st Degree AVB
Symptoms: Automatic Trigger
Activities: None Indicated
HR: 20

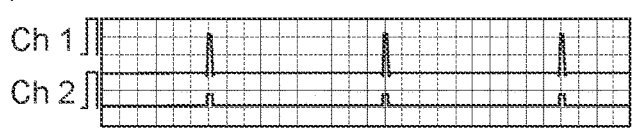

Date: 07/18/2016 | 22:02:24 PDT
Findings: urgent - representing
Symptoms: Automatic Trigger
Activities: None Indicated
HR: 30

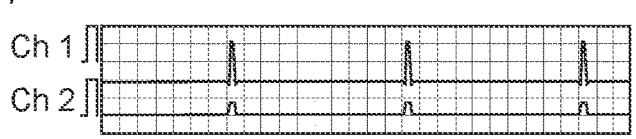

Date: 07/18/2016 | 23:08:35 PDT
Findings: Ventricular Tachycardia
Symptoms: Automatic Trigger
Activities: None Indicated
HR: 69

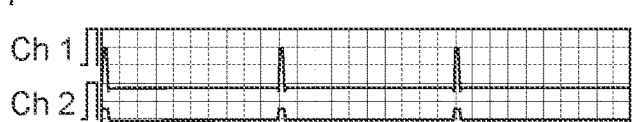

Date: 07/18/2016 | 23:08:39 PDT
Findings: Ventricular Tachycardia
Symptoms: Automatic Trigger
Activities: None Indicated
HR: 130

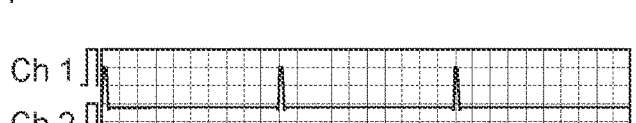

FIG. 15

Strip Summary

Date: 07/18/2016 | 23:19:37 PDT  802
Findings: Advanced Heart Block
Symptoms: Automatic Trigger
Activities: None Indicated
HR: 60

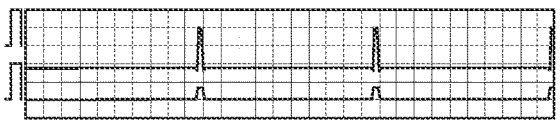

Date: 07/18/2016 | 23:19:41 PDT
Findings: h Advanced Heart Block
Symptoms: Automatic Trigger
Activities: None Indicated
HR: 81

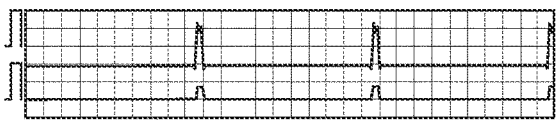

Date: 07/18/2016 | 23:30:39 PDT
Findings: 8 Second Pause
Symptoms: Automatic Trigger
Activities: None Indicated
HR: 30

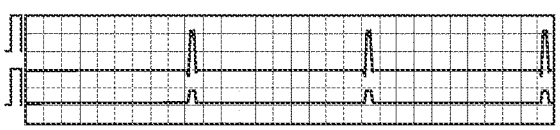

Date: 07/18/2016 | 23:30:42 PDT
Findings: Pauses
Symptoms: Automatic Trigger
Activities: None Indicated
HR: 30

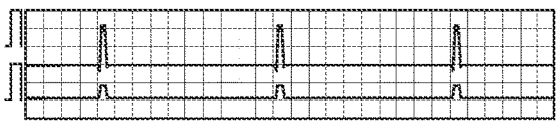

Date: 07/18/2016 | 23:30:43 PDT
Findings: 9 Second Pause
Symptoms: Automatic Trigger
Activities: None Indicated
HR: 20

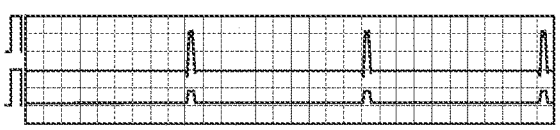

FIG. 16

Strip Summary

Date: 07/18/2016 | 23:41:41 PDT  802
Findings: Supraventricular Tachycardia
Symptoms: Automatic Trigger
Activities: None Indicated
HR: 30

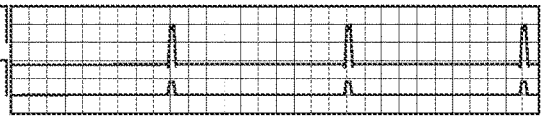

Date: 07/18/2016 | 23:41:41 PDT
Findings: PIE
Symptoms: Automatic Trigger
Activities: None Indicated
HR: 30

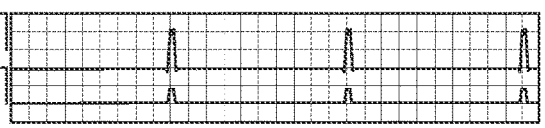

Date: 07/18/2016 | 23:52:43 PDT
Findings: Atrial Fibrillation
Symptoms: Automatic Trigger
Activities: None Indicated
HR: 30

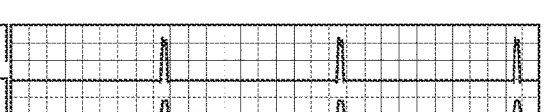

Date: 07/19/2016 | 05:12:39 PDT
Findings: test
Symptoms: Automatic Trigger
Activities: None Indicated
HR: 30

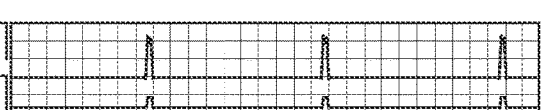

Date: 07/19/2016 | 06:29:54 PDT
Findings: Supraventricular Tachycardia
Symptoms: Automatic Trigger
Activities: None Indicated
HR: 30

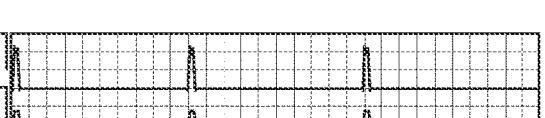

FIG. 17

Strip Summary

Date: 07/19/2016 | 12:20:00 PDT — 802
Findings: adh Urgent - representing
Symptoms: Automatic Trigger
Activities: None Indicated
HR: 30

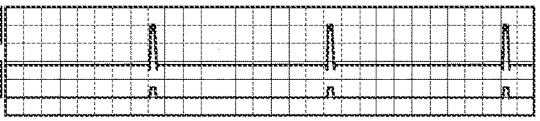

---

Date: 07/19/2016 | 12:20:02 PDT
Findings: adh Advanced Heart Block
Symptoms: Automatic Trigger
Activities: None Indicated
HR: 30

---

Date: 07/19/2016 | 12:20:05 PDT
Findings: Advanced Heart Block
Symptoms: Automatic Trigger
Activities: None Indicated
HR: 78

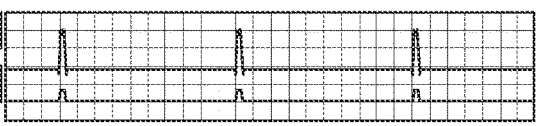

---

Date: 07/19/2016 | 13:18:04 PDT
Findings: Ventricular Tachycardia
Symptoms: Automatic Trigger
Activities: None Indicated
HR: 156

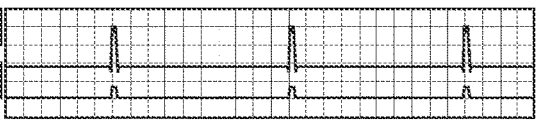

---

Date: 07/19/2016 | 13:38:32 PDT
Findings: Atrial Fibrillation
Symptoms: Automatic Trigger
Activities: None Indicated
HR: 136

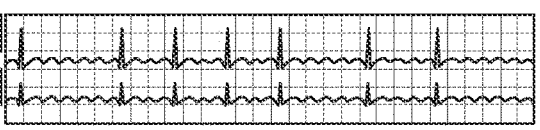

FIG. 18

Strip Summary

Date: 07/19/2016 | 16:51:51 PDT — 802
Findings: 12 Second Pause
Symptoms: Automatic Trigger
Activities: None Indicated
HR: 20

Date: 07/19/2016 | 16:59:51 PDT
Findings: 1st Degree AVB
Symptoms: Automatic Trigger
Activities: None Indicated
HR: 20

Date: 07/20/2016 | 01:17:29 PDT
Findings: PIE
Symptoms: Automatic Trigger
Activities: None Indicated
HR: 160

Date: 07/20/2016 | 04:59:11 PDT
Findings: Advanced Heart Block
Symptoms: Automatic Trigger
Activities: None Indicated
HR: 40

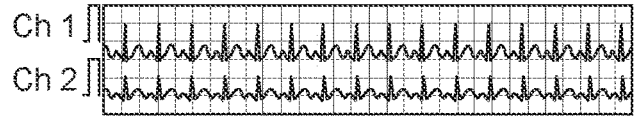

Date: 07/20/2016 | 04:59:11 PDT
Findings: 8 Second Pause
Symptoms: Automatic Trigger
Activities: None Indicated
HR: 160

FIG. 19

Strip Summary

Date: 07/20/2016 | 04:59:13 PDT — 802
Findings: PIE
Symptoms: Automatic Trigger
Activities: None Indicated
HR: 160

Date: 07/20/2016 | 04:59:14 PDT
Findings: Ventricular Tachycardia
Symptoms: Automatic Trigger
Activities: None Indicated
HR: 55

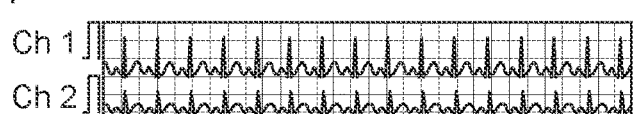

Date: 07/20/2016 | 04:59:17 PDT
Findings: Atrial Fibrillation
Symptoms: Automatic Trigger
Activities: None Indicated
HR: 88

Date: 07/21/2016 | 10:46:49 PDT
Findings: Advanced Heart Block
Symptoms: Short of Breath, Symtom other than listed
Activities: Heavy Activity
HR: 30

Date: 07/21/2016 | 10:46:52 PDT
Findings: 2nd Degree Heart Block Type 2
Symptoms: Short of Breath, Symtom other than listed
Activities: Heavy Activity
HR: 33

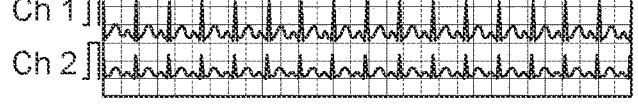

FIG. 20

Strip Summary

802

---

Date: 07/21/2016 | 15:47:57 PDT
Findings: Atrial Fibrillation
Symptoms: Chest Pain
Activities: Moderate Activity
HR: 195

Ch 1
Ch 2

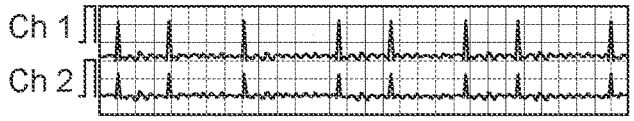

---

Date: 07/21/2016 | 15:48:00 PDT
Findings: test representing
Symptoms: Chest Pain
Activities: Moderate Activity
HR: 31

Ch 1
Ch 2

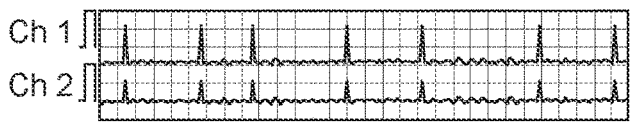

---

Date: 07/22/2016 | 14:46:37 PDT
Findings: test
Symptoms: Short of Breath,
Symtom other than listed
Activities: Heavy Activity
HR: 195

Ch 1
Ch 2

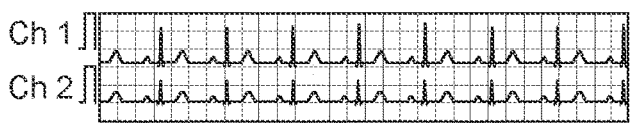

---

Date: 07/22/2016 | 14:46:41 PDT
Findings: test
Symptoms: Short of Breath,
Symtom other than listed
Activities: Heavy Activity
HR: 200

Ch 1
Ch 2

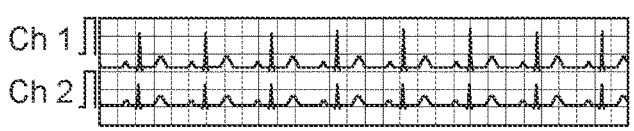

---

Date: 07/22/2016 | 14:47:19 PDT
Findings: Advanced Heart Block
Symptoms: Short of Breath,
Symtom other than listed
Activities: Heavy Activity
HR: 100

Ch 1
Ch 2

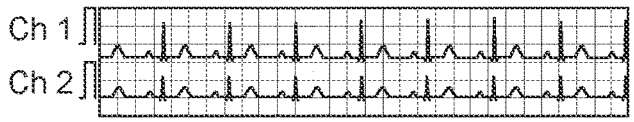

Strip Summary

802

Date: 07/22/2016 | 14:47:30 PDT
Findings: Supraventricular Tachycardia
Symptoms: Short of Breath,
 Symtom other than listed
Activities: Heavy Activity
HR: 180

Ch 1
Ch 2 

Date: 07/22/2016 | 16:59:18 PDT
Findings: Supraventricular Tachycardia
Symptoms: Automatic Trigger
Activities: None Indicated
HR: 130

Ch 1
Ch 2 

Date: 07/22/2016 | 17:00:09 PDT
Findings: test
Symptoms: Automatic Trigger
Activities: None Indicated
HR: 220

Ch 1
Ch 2 

Date: 07/23/2016 | 17:00:09 PDT
Findings: Atrial Fibrillation
Symptoms: Automatic Trigger
Activities: None Indicated
HR: 80

Ch 1
Ch 2 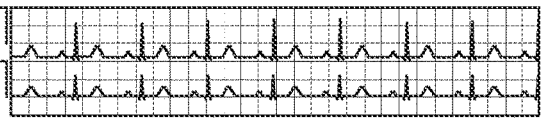

Date: 07/24/2016 | 12:30:02 PDT
Findings: 13 Second Pause
Symptoms: Automatic Trigger
Activities: None Indicated
HR: 66

Ch 1
Ch 2 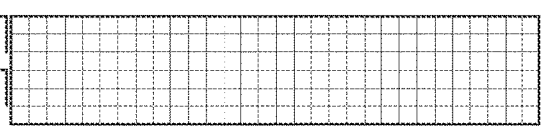

FIG. 22

Strip Summary 802

Date: 07/24/2016 | 12:30:03 PDT
Findings: 13 Second pause
Symptoms: Automatic Trigger
Activities: None Indicated
HR: 87

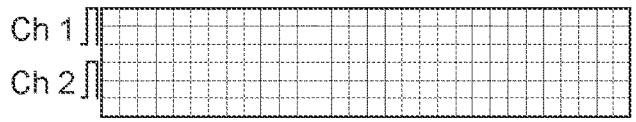

Date: 07/25/2016 | 17:26:40 PDT
Findings: Ventricular Tachycardia
Symptoms: Heart Racing, Symtom other than listed
Activities: Heavy Activity
HR: 210

Date: 07/25/2016 | 18:17:29 PDT
Findings: Atrial Fibrillation
Symptoms: Automatic Trigger
Activities: None Indicated
HR: 199

Date: 07/25/2016 | 18:17:31 PDT
Findings: Atrial Fibrillation
Symptoms: Automatic Trigger
Activities: None Indicated
HR: 201

Date: 07/27/2016 | 16:17:14 PDT
Findings: Ventricular Tachycardia
Symptoms: Automatic Trigger
Activities: None Indicated
HR: 24

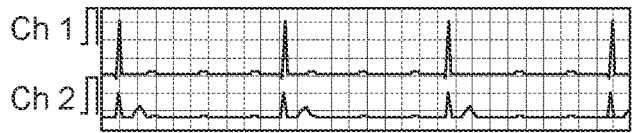

FIG. 23

Strip Summary

---

Date: 07/28/2016 | 10:59:31 PDT  802
Findings: 1st Degree AVB
Symptoms: Skipped Beat, Light Headed, Short of Breath, Heart Racing, Fainted, Dizzy, Chest Pain, Symptom other than listed
Activities: Moderate Activity
HR: 13

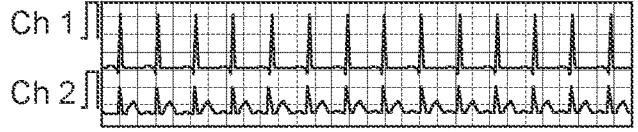

---

Date: 07/28/2016 | 10:59:37 PDT
Findings: Advanced Heart Block
Symptoms: Skipped Beat, Light Headed, Short of Breath, Heart Racing, Fainted, Dizzy, Chest Pain, Symptom other than listed
Activities: Moderate Activity
HR: 12

---

Date: 07/28/2016 | 10:59:43 PDT
Findings: 2nd Degree AVB
Symptoms: Skipped Beat, Light Headed, Short of Breath, Heart Racing, Fainted, Dizzy, Chest Pain, Symptom other than listed
Activities: Moderate Activity
HR: 14

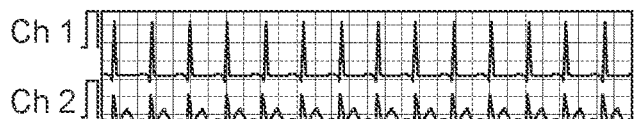

---

Date: 07/28/2016 | 10:59:49 PDT
Findings: 2nd Degree AVB, Type 1, Wenckebach
Symptoms: Skipped Beat, Light Headed, Short of Breath, Heart Racing, Fainted, Dizzy, Chest Pain, Symptom other than listed
Activities: Moderate Activity
HR: 11

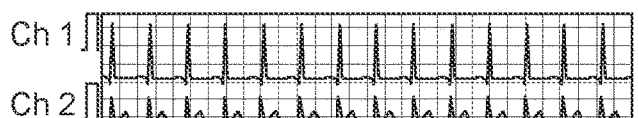

---

Date: 07/28/2016 | 10:59:55 PDT
Findings: 2nd Degree AVB, Type 2
Symptoms: Skipped Beat, Light Headed, Short of Breath, Heart Racing, Fainted, Dizzy, Chest Pain, Symptom other than listed
Activities: Moderate Activity
HR: 17

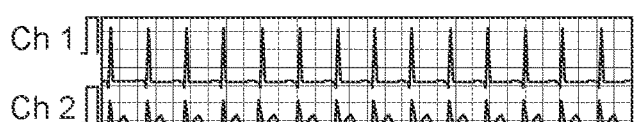

FIG. 24

Strip Summary

---

Date: 07/28/2016 | 11:00:01 PDT
Findings: 2:1 Conduction
Symptoms: Skipped Beat, Light Headed, Short of Breath, Heart Racing, Fainted, Dizzy, Chest Pain, Symptom other than listed
Activities: Moderate Activity
HR: 18

802

---

Date: 07/28/2016 | 11:00:07 PDT
Findings: test
Symptoms: Skipped Beat, Light Headed, Short of Breath, Heart Racing, Fainted, Dizzy, Chest Pain, Symptom other than listed
Activities: Moderate Activity
HR: 11

---

Date: 07/28/2016 | 11:00:13 PDT
Findings: Atrial Bigeminy
Symptoms: Skipped Beat, Light Headed, Short of Breath, Heart Racing, Fainted, Dizzy, Chest Pain, Symptom other than listed
Activities: Moderate Activity
HR: 10

---

Date: 07/28/2016 | 11:00:19 PDT
Findings: Ventricular Tachycardia
Symptoms: Skipped Beat, Light Headed, Short of Breath, Heart Racing, Fainted, Dizzy, Chest Pain, Symptom other than listed
Activities: Moderate Activity
HR: 111

---

Date: 07/28/2016 | 11:00:25 PDT
Findings: 12 Second Pause
Symptoms: Skipped Beat, Light Headed, Short of Breath, Heart Racing, Fainted, Dizzy, Chest Pain, Symptom other than listed
Activities: Moderate Activity
HR: 140

FIG. 25

Strip Summary                                               802

Date: 07/28/2016 | 11:00:31 PDT
Findings: Supraventricular Tachycardia
Symptoms: Skipped Beat, Light Headed, Short of Breath, Heart Racing, Fainted, Dizzy, Chest Pain, Symptom other than listed
Activities: Moderate Activity
HR: 199

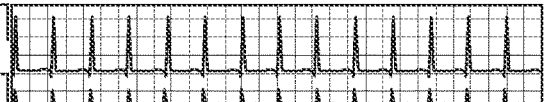

Date: 07/28/2016 | 11:01:01 PDT
Findings: Advanced Heart Block
Symptoms: Skipped Beat, Light Headed, Short of Breath, Heart Racing, Fainted, Symptom other than listed
Activities: Moderate Activity
HR: 19

Date: 07/28/2016 | 11:06:34 PDT
Findings: Atrial Fibrillation
Symptoms: Skipped Beat, Light Headed, Short of Breath, Heart Racing, Fainted, Dizzy, Chest Pain, Symptom other than listed
Activities: Heavy Activity
HR: 211

Date: 07/30/2016 | 14:37:04 PDT
Findings: Ventricular Tachycardia
Symptoms: Automatic Trigger
Activities: None Indicated
HR: 34

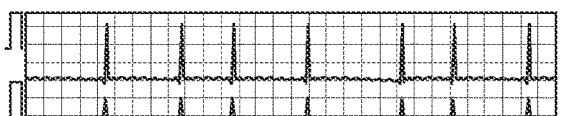

Date: 07/31/2016 | 14:38:04 PDT
Findings: Atrial Fibrillation
Symptoms: Automatic Trigger
Activities: None Indicated
HR: 163

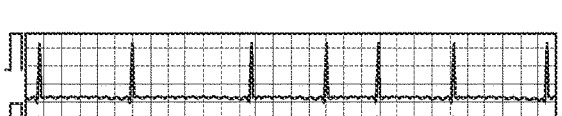

FIG. 26

Strip Summary

Date: 08/01/2016 | 14:39:05 PDT
Findings: Atrial Fibrillation
Symptoms: Automatic Trigger
Activities: None Indicated
HR: 164

Date: 08/02/2016 | 10:50:01 PDT
Findings: Atrial Fibrillation
Symptoms: Short of Breath, Symptom other than listed
Activities: Heavy Activity
HR: 168

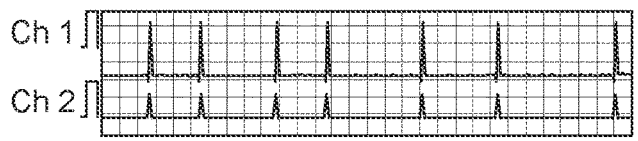

Date: 08/02/2016 | 10:50:09 PDT
Findings: 12 Second Pause
Symptoms: Symptom other than listed
Activities: Heavy Activity
HR: 75

Date: 08/02/2016 | 10:50:13 PDT
Findings: Advanced Heart Block
Symptoms: Symptom other than listed
Activities: Heavy Activity
HR: 11

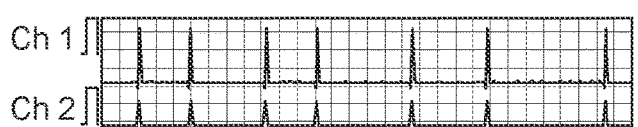

Date: 08/02/2016 | 10:50:17 PDT
Findings: Atrial Fibrillation
Symptoms: Symptom other than listed
Activities: Heavy Activity
HR: 199

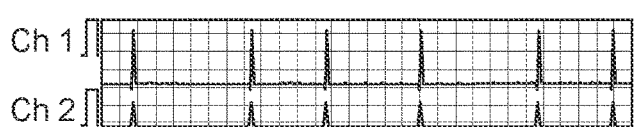

FIG. 27

Strip Summary                                802

Date: 08/02/2016 | 10:50:18 PDT
Findings: Ventricular Tachycardia
Symptoms: Symptom other than listed
Activities: Heavy Activity
HR: 201

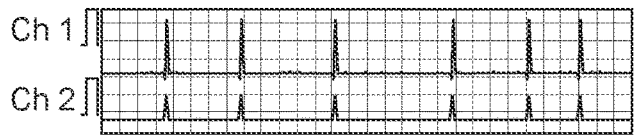

Date: 08/02/2016 | 10:50:28 PDT
Findings: Supraventricular Tachycardia
Symptoms: Symptom other than listed
Activities: Heavy Activity
HR: 222

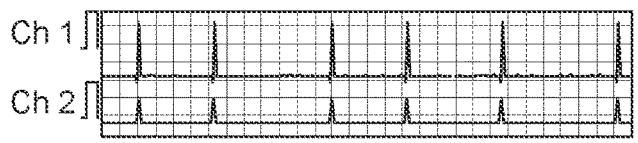

Date: 08/02/2016 | 10:50:37 PDT
Findings: 2nd Degree AVB
Symptoms: Symptom other than listed
Activities: Heavy Activity
HR: 11

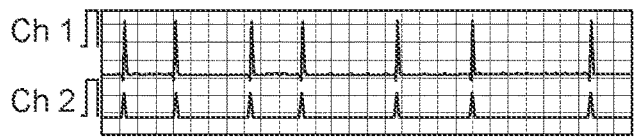

Date: 08/02/2016 | 10:50:51 PDT
Findings: 3rd Degree AVB
Symptoms: Symptom other than listed
Activities: Heavy Activity
HR: 11

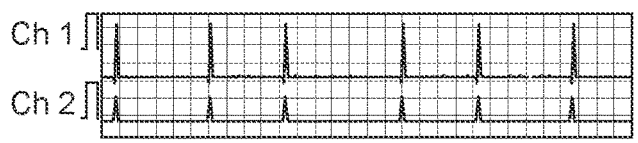

Date: 08/02/2016 | 10:50:58 PDT
Findings: 1st Degree AVB
Symptoms: Symptom other than listed
Activities: Heavy Activity
HR: 11

FIG. 28

Strip Summary

Date: 08/02/2016 | 14:40:05 PDT — 802
Findings: Atrial Fibrillation
Symptoms: Automatic Trigger
Activities: None Indicated
HR: 155

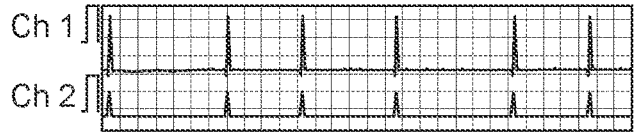

Date: 08/03/2016 | 12:04:21 PDT
Findings: Atrial Fibrillation
Symptoms: Light Headed, Short of Breath, Heart Racing, Chest Pain,
Activities: Heavy Activity
HR: 150

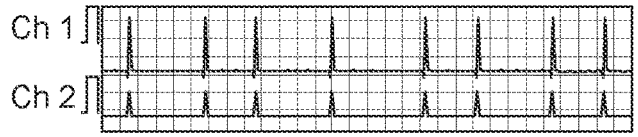

Date: 08/03/2016 | 14:41:06 PDT
Findings: Atrial Fibrillation
Symptoms: Automatic Trigger
Activities: None Indicated
HR: 58

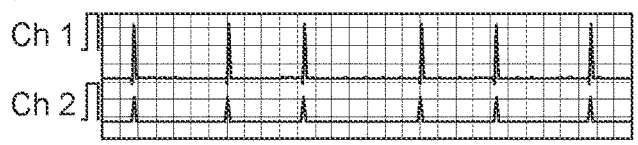

Date: 08/04/2016 | 00:58:59 PDT
Findings: Ventricular Tachycardia
Symptoms: Automatic Trigger
Activities: None Indicated
HR: 193

Date: 08/04/2016 | 00:59:04 PDT
Findings: Ventricular Tachycardia
Symptoms: Automatic Trigger
Activities: None Indicated
HR: 152

FIG. 29

Strip Summary

802

Date: 08/04/2016 | 00:59:41 PDT
Findings: Ventricular Tachycardia
Symptoms: Automatic Trigger
Activities: None Indicated
HR: 203

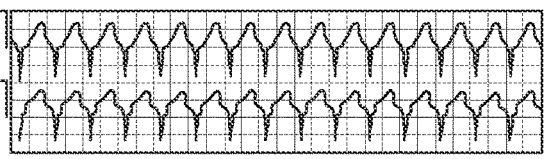

Date: 08/04/2016 | 00:59:47 PDT
Findings: Supraventricular Tachycardia
Symptoms: Automatic Trigger
Activities: None Indicated
HR: 212

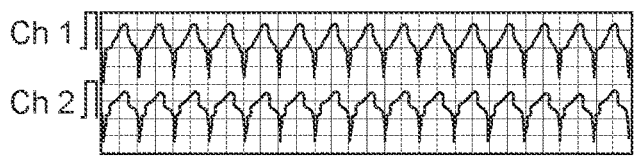

Date: 08/05/2016 | 10:57:04 PDT
Findings: Ventricular Tachycardia
Symptoms: Automatic Trigger
Activities: None Indicated
HR: 152

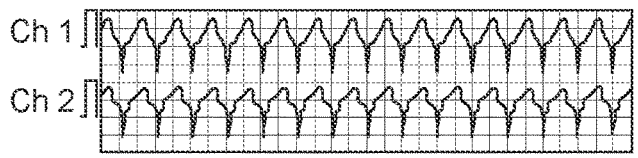

Date: 08/05/2016 | 10:57:07 PDT
Findings: Urgent
Symptoms: Heart Racing, Symptom other than listed
Activities: Heavy Activity
HR: 151

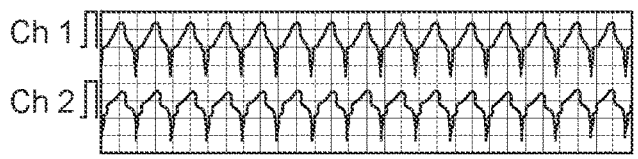

FIG. 30

END OF SERVICE SUMMARY REPORT FOR MOBILE CARDIAC OUTPATIENT TELEMETRY

CROSS REFERENCE TO RELATED APPLICATIONS

This application is a continuation of U.S. application Ser. No. 15/678,594, filed Aug. 16, 2017, now allowed, which claims priority to U.S. Provisional Application No. 62/375,738, filed on Aug. 16, 2016, the content of which is incorporated herein by reference in its entirety.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Cardiac arrhythmia includes a group of conditions in which a heartbeat is irregular. For example, the heartbeat may be too fast (tachycardia) or too slow (bradycardia). Atrial fibrillation (AF) is the most common type of arrhythmia. During AF, one or both of the heart's upper chambers (atria) do not contract properly, thus impeding the pumping of blood into the lower chambers (ventricles). Cardiac arrhythmia, such as AF, affects millions of people and may result in palpitations, lightheadedness, shortness of breath, fainting (syncope), chest pain, stroke, heart failure, and cardiac arrest. In some patients, cardiac arrhythmia events, such as periods of time during which the heartbeat is too fast or too slow, do not occur frequently. Instead, cardiac arrhythmia events may occur infrequently, such as every few days.

Cardiac arrhythmia events can be detected by measuring a patient's electrocardiogram (ECG), which is a recording of the electrical activity of the heart. To detect cardiac arrhythmia events that occur infrequently, it may be impractical to require a patient to undergo ECG recording at a hospital for the length of time required to detect an event. Instead, it may be desirable to record the patient's ECG outside of the hospital. Thus, devices for recording ECG data that a patient can wear during normal life activities have been developed. These devices may include electrodes for measuring ECG data, a sensor to store the ECG data, and a means for enabling the user to wear the sensor, such as a lanyard worn around the neck. Collected ECG data may be obtained by a physician through different methods. For example, the device can transmit the ECG data directly to the physician over a cellular or wireless network. Such a system is called mobile cardiac outpatient telemetry (MCOT).

During monitoring with an MCOT device, algorithms in the device may analyze collected ECG data for findings. Examples of findings are atrial fibrillation, heart block, pause, supraventricular tachycardia, and ventricular tachycardia. During monitoring with an MCOT device, a patient may have the ability to record a symptom that the patient is experiencing during a given time period. For example, the MCOT device may have a display from which the patient can choose a symptom from a menu of symptom options. The recorded symptom may then be saved along with data collected at the time when the symptom is recorded for inclusion in the patient report. Examples of symptoms are heart racing, shortness of breath, skipped beat, chest pain, light headedness, fainting, and dizziness. Data collected in connection with a recorded symptom may be considered "symptomatic." During monitoring with an MCOT device, a patient may not experience a symptom, but algorithms analyzing the collected data may detect a finding in the collected data and save the data along with an indication that the patient was asymptomatic. Such data may be considered "asymptomatic" and/or "auto triggered." During monitoring with an MCOT device, a patient may also be able to record a certain level of activity (e.g., heavy activity) that the patient was engaging in at a certain time in a similar manner as recording symptoms.

Because MCOT monitoring periods can be long (for example, 5 days, 10 days, 15 days, 20 days, 25 days, 30 days, etc.), the amount of data collected by the MCOT device can be large. To ensure that the collected data can be used productively by a physician, it is important to filter the collected data for presentation to the physician on a report in a manner that helps the physician interpret the data efficiently and effectively. Existing priority data filters and reports suffer from multiple drawbacks. For example, in some patient reports, priority data filters do not retain sufficiently organized information, and/or do not retain a sufficient portion of priority information for inclusion on the reports' first pages, making it necessary to search through multiple pages of the reports for priority information. In some patient reports, existing priority data filters retain graphs and strips for the first page of the report, which is typically the focus of a physician reviewing the report. Therefore, the first page of the report becomes overburdened with graphs and strips that consume space. As used herein, "strips" refer to images of ECG data that may be presented to a physician in a report.

Specific examples of patient reports in the prior art are the patient reports produced by Medicomp (see FIGS. 1-3), MediLynx (FIG. 4), and iRhythm (FIG. 5). The first page of each patient report has a number of graphs, charts, and/or strips which occupy space on the first page that could be used for other types of information.

A further problem in processing collected ECG data for a patient report is providing accurate high heart rate information. In preparing some patient reports, algorithms that calculate high heart rate from collected ECG data may produce a high heart rate value that is corrupted by artifacts. A further problem in processing collected ECG data for a patient report is providing accurate low heart rate information. In preparing some patient reports, algorithms that calculate low heart rate from collected ECG data may produce a low heart rate value that is corrupted by a pause event.

SUMMARY

The data filter and report described herein have multiple benefits that address these drawbacks. The priority data filter retains priority information from collected MCOT data that a physician needs for interpreting the collected data, and this priority information is presented on the first page of the report, which is typically the focus of a physician reviewing the report. This is helpful because the physician does not need to search through multiple pages of the report to find important information needed for interpreting the collected data. The priority data filter does not retain graphs or strips for inclusion on the first page of the report. This is helpful because graphs and strips occupy a large amount of space, and therefore including graphs and strips on the first page may not be the most efficient use of space on the first page.

For example, while a strip may show detailed information about one event, the space occupied by that strip can instead be used for showing other priority information retained by the priority data filter, such as summary information about multiple events. The report also organizes information from the collected data by category for presentation in the report. For example, information about AF is organized and presented in its own section of the report and information about HR is organized and presented in its own section of the report. This is helpful because the physician, when considering, for example, AF, will have the AF information in one section and will not have to search through multiple pages of the report to find information about AF. Furthermore, organizing information in the report by category means that the information is presented in a more sensible and understandable manner and may help the physician interpret the data efficiently and effectively as the physician reads through the report. The patient report also places important information, such as summary information regarding AF and HR, near the front of the report, while keeping other information such as strips towards the back of the report.

In preparing the patient report discussed herein, algorithms for calculating high heart rate may reduce the chance of including a high heart rate value that is inaccurate due to artifacts. To accomplish this, the patient report may show the highest heart rate calculated by the algorithms that is associated with data that has an acceptably low number of artifacts, even if the other data that contains artifacts indicates a higher heart rate. Additionally, in preparing the patient report discussed herein, algorithms for calculating low heart rate may reduce the chance of including a low heart rate value that is inaccurate due to a pause event. To accomplish this, the algorithms may recognize pause events and prevent the pause event from inclusion in calculations of low heart rate.

In one aspect, a method for filtering ECG data includes receiving ECG data of a patient, generating an ECG report comprising a plurality of pages, presenting, on a first page of the plurality of pages: information identifying the patient, monitoring summary information including an indication of a total duration of a monitoring period, heart rate summary information including an average heart rate, a fastest heart rate, and a slowest heart rate, representative arrhythmia summary information including a count of ECG strips containing each of a plurality of types of cardiac arrhythmia, and atrial fibrillation summary information including an indication of atrial fibrillation burden during the monitoring period. The first page does not include an ECG strip.

In some implementations, the first page does not include a graph of ECG data. In certain implementations, the method also includes excluding a portion of the ECG data from calculation of the lowest heart rate if the portion includes a pause event. In some implementations, the method also includes receiving an artifact threshold and excluding a portion of the ECG data from calculations of the highest heart rate if the portion includes an amount of artifact that exceeds the artifact threshold.

In certain implementations, the representative arrhythmia summary information includes the date, time, and heart rate corresponding to: a fastest atrial fibrillation, a fastest supraventricular tachycardia, a longest pause, a slowest heart block, and a fastest ventricular tachycardia. In some implementations, the representative arrhythmia summary information includes a count of ECG strips containing atrial fibrillation, a count of ECG strips containing heart block, a count of ECG strips containing pause, a count of ECG strips containing supraventricular tachycardia, and a count of ECG strips containing ventricular tachycardia. In certain implementations, symptomatic arrhythmia events are counted separately from asymptomatic arrhythmia events. In some implementations, the representative arrhythmia summary information includes, for symptomatic arrhythmia events, an indication of symptoms associated with the symptomatic arrhythmia events as recorded by the patient.

In some implementations, the method also includes presenting event summary information on the first page, and the event summary information includes an indication of an earliest page on which ECG strips are presented. In certain implementations, the event summary information includes an indication of a total number of ECG strips presented in the report. In some implementations, the monitoring summary information further includes a number of days for which a monitoring device was prescribed to the patient, a number of days in which monitoring occurred, a baseline date, and an end date. In certain implementations, the heart rate summary information includes the date and time at which the highest heart rate occurred and the date and time at which the lowest heart rate occurred. In some implementations, the atrial fibrillation summary information includes total time in atrial fibrillation, number of atrial fibrillation episodes, longest atrial fibrillation, highest heart rate during atrial fibrillation, lowest heart rate during atrial fibrillation, average heart rate during atrial fibrillation, highest heart rate not during atrial fibrillation, lowest heart rate not during atrial fibrillation, and average heart rate not during atrial fibrillation.

In certain implementations, the method also includes presenting, on a second page, a histogram of atrial fibrillation duration, a histogram of atrial fibrillation onset, and an indication of daily atrial fibrillation burden for each of a plurality of days in the monitoring period. In some implementations, the method also includes presenting, on the second page, total time in atrial fibrillation, number of atrial fibrillation episodes, longest atrial fibrillation, highest heart rate during atrial fibrillation, lowest heart rate during atrial fibrillation, average heart rate during atrial fibrillation, highest heart rate not during atrial fibrillation, lowest heart rate not during atrial fibrillation, and average heart rate not during atrial fibrillation.

In another aspect, a system for filtering ECG data includes a processor and computer-readable memory storing instructions which, when executed by the processor, cause the processor to perform operations. The operations include receiving ECG data of a patient, generating an ECG report comprising a plurality of pages, and presenting, on a first page of the plurality of pages: information identifying the patient, monitoring summary information, heart rate summary information, representative arrhythmia summary information, and atrial fibrillation summary information. The first page does not include an ECG strip. The monitoring summary information includes an indication of a total duration of a monitoring period, the heart rate summary information includes an average heart rate, a fastest heart rate, and a slowest heart rate. The representative arrhythmia summary information includes a count of ECG strips containing each of a plurality of types of cardiac arrhythmia. The atrial fibrillation summary information includes an indication of atrial fibrillation burden during the monitoring period.

In some implementations, the first page does not include a graph of ECG data. In certain implementations, the operations also include excluding a portion of the ECG data from calculation of the lowest heart rate if the portion includes a pause event. In some implementations, the operations also include receiving an artifact threshold and excluding a portion of the ECG data from calculations of the highest heart rate if the portion includes an amount of artifact that exceeds the artifact threshold. In certain implementations, the representative arrhythmia summary information includes the date, time, and heart rate corresponding to: a fastest atrial fibrillation, a fastest supraventricular tachycardia, a longest pause, a slowest heart block, and a fastest ventricular tachycardia.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF DRAWINGS

The foregoing and other objects and advantages will be apparent upon consideration of the following detailed description, taken in conjunction with the accompanying drawings, in which like reference characters refer to like parts throughout, and in which:

FIGS. 4A and 4B show a first page of a patient report in the prior art, produced by MediLynx;

FIGS. 5A and 5B show a first page of a patient report in the prior art, produced by iRhythm;

FIGS. 6A and 6B show an illustrative first page 100 of an end of service summary report in accordance with some embodiments of the disclosure;

FIGS. 9A and 9B show an illustrative page 400 of an end of service summary report in accordance with some embodiments of the disclosure;

FIGS. 10A and 10B show an illustrative page 500 of an end of service summary report in accordance with some embodiments of the disclosure;

FIGS. 11A and 11B show an illustrative page 600 of an end of service summary report in accordance with some embodiments of the disclosure;

FIGS. 12A and 12B show an illustrative page 700 of an end of service summary report in accordance with some embodiments of the disclosure;

FIGS. 13A and 13B show an illustrative page 800 of an end of service summary report in accordance with some embodiments of the disclosure; and FIGS. 14-30 show further illustrative pages of the end of service summary report in accordance with some embodiments of the disclosure

DETAILED DESCRIPTION

Figure 1A:
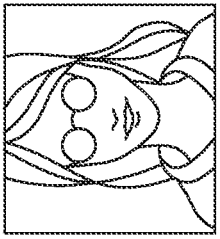
FIGS. 1A and 1B, 2A and 2B, and 3A and 3B show first pages of patient reports in the prior art, produced by Medicomp.
Figure 1B:
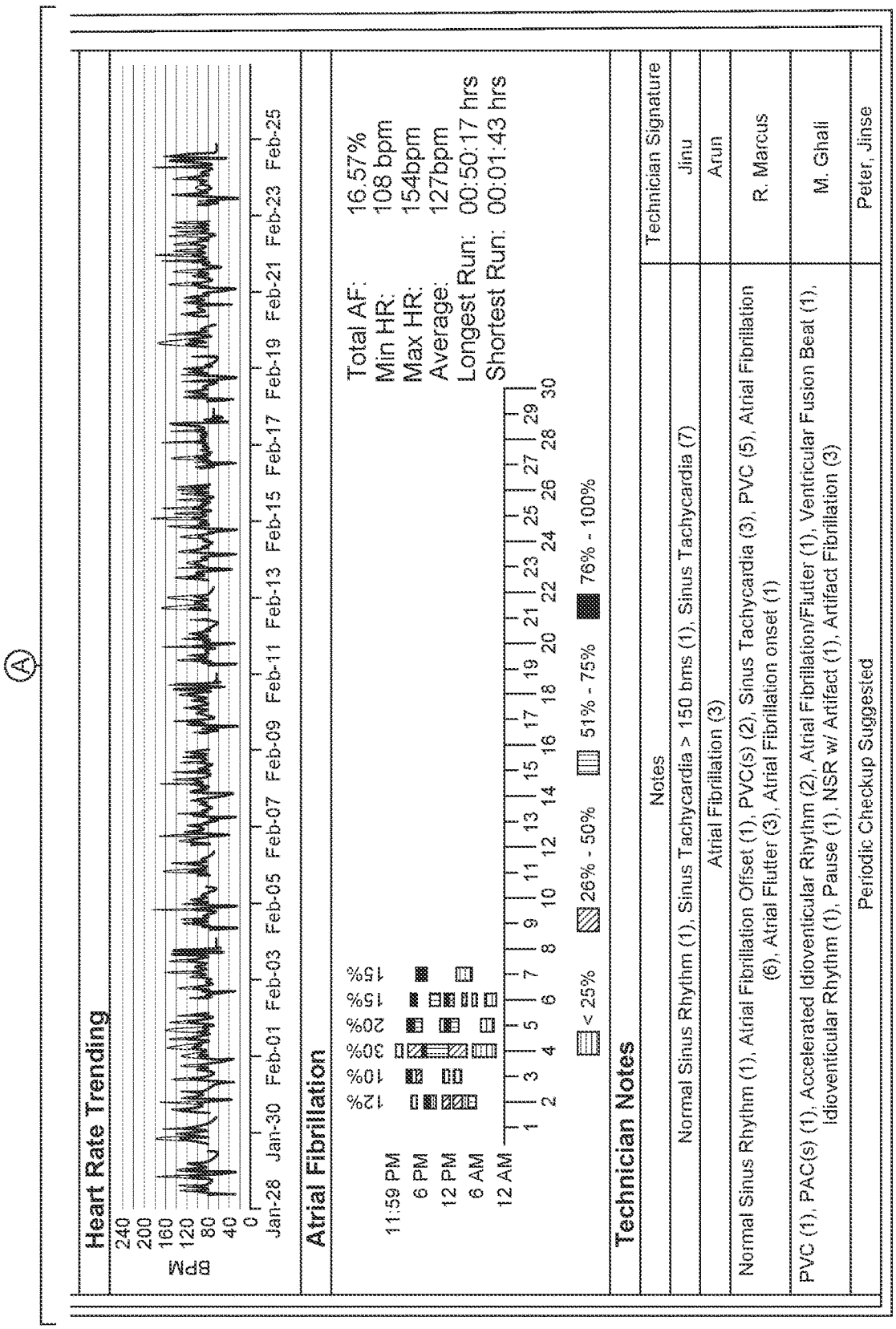
Figure 2A:
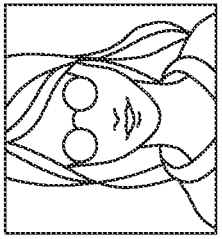
Figure 2B:
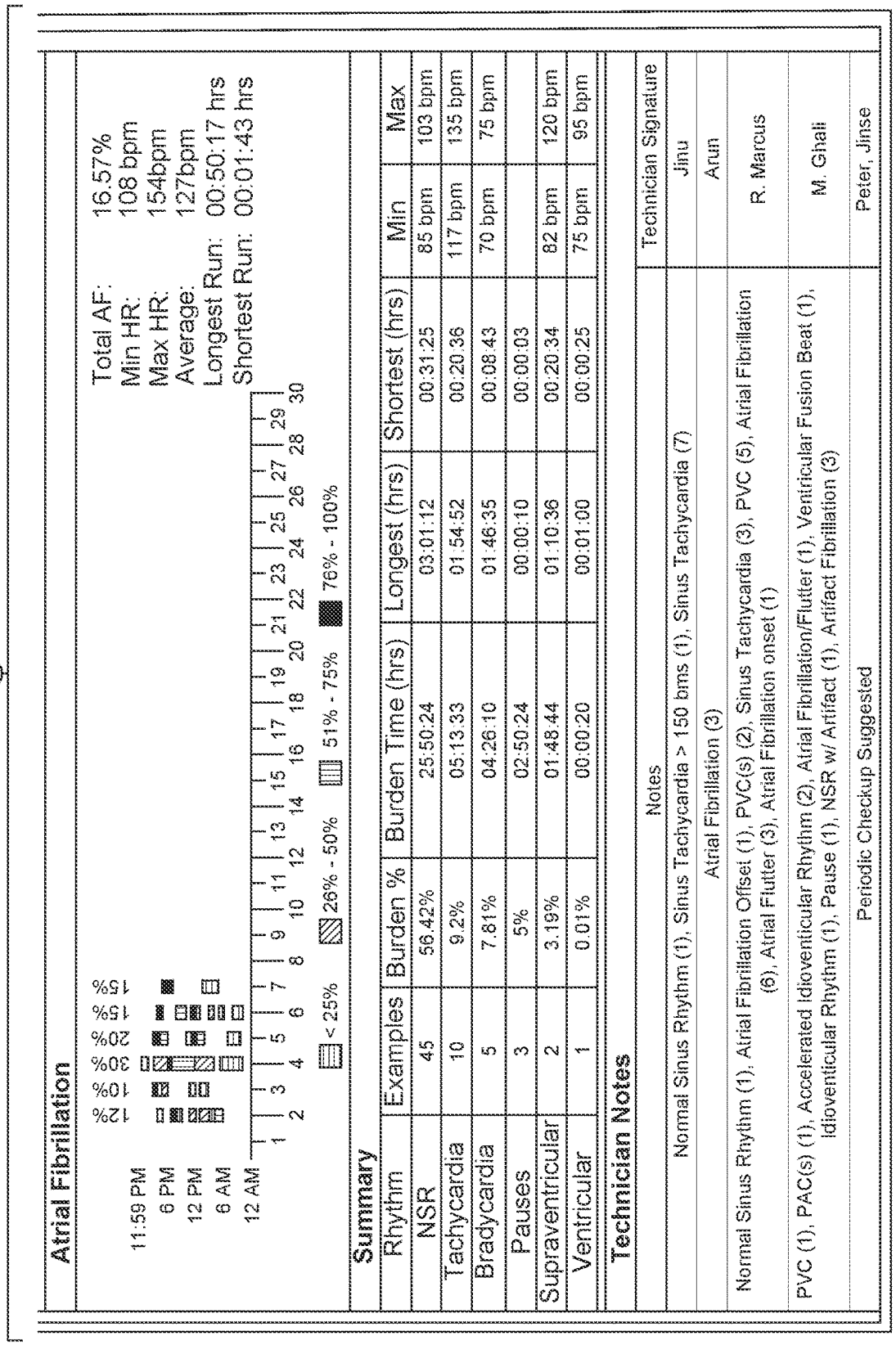
Figure 3A:
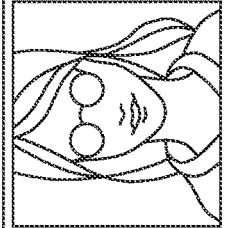
Figure 3B:
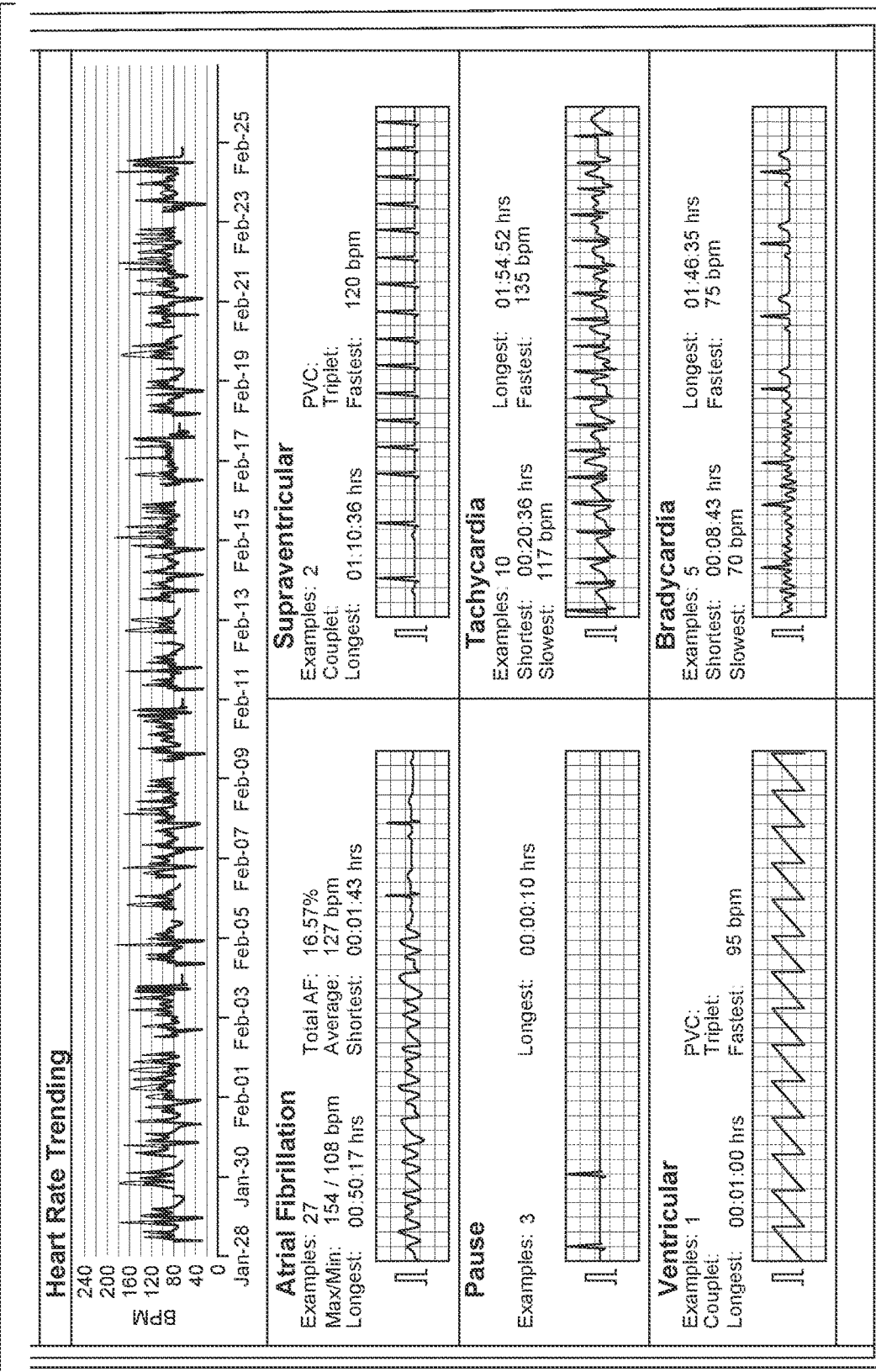

To provide an overall understanding of the data filter and end of service summary report for mobile cardiac outpatient telemetry, certain illustrative embodiments will be described. Although the embodiments and features described herein are specifically described for use in connection with data filters and end of service summary reports for mobile cardiac outpatient telemetry, it will be understood that all the features outlined below may be combined with one another in any suitable manner and may be adapted and applied to other types of patient reports for other types of monitoring.

FIGS. 1-5 are discussed above in the Background.

FIGS. 6A and 6B show an illustrative first page 100 of an end of service summary report in accordance with some embodiments of the disclosure. A priority data filter analyzing data collected by the MCOT device retains priority information from the collected data. The priority information retained by the priority data filter is presented on the first page 100 and will be discussed below in relation to various sections of the first page 100 that contain the priority information. The priority information is included in a patient and physician information section 102, a monitoring summary section 104, an event summary section 106, a heart rate (HR) summary section 108, a representative arrhythmia summary section 110, an atrial fibrillation (AF) summary section 112, and a physician comments section 114.

The patient and physician information section 102 includes information retained by the priority data filter about the patient's name, the patient's date of birth, the patient's gender, the patient's phone number, the patient's medical record, the patient's diagnosis, the notification physician's name and address, the ordering physician's name, and the referring physician's name.

The monitoring summary section 104 includes information retained by the priority data filter about the total time period in which monitoring occurred, the number of days for which the MCOT device was prescribed to the patient, the number of days in which monitoring occurred, a baseline date, and an end date.

The event summary section 106 includes information retained by the priority data filter about the total number of strips present in the report, the number of strips in which the patient was symptomatic, the number of strips in which show emergent/urgent findings. The event summary section 106 includes an indication of on which page of the report strips begin to be presented. This indication can be helpful in avoiding a physician needing to search through an entire report in order to find strips.

The HR summary section 108 includes information retained by the priority data filter about the value of the highest heart rate during the monitoring period, the date and time at which the highest heart rate occurred, the value of the lowest heart rate during the monitoring period, the date and time at which the lowest heart rate occurred, and the average heart rate from the monitoring period.

The HR summary section 108 includes an indication of on which page of the report information about daily heart rate and strips relating to high and low heart rate are presented. As discussed above, the first page 100 does not contain strips, in order to conserve space on the first page 100. However, a physician may wish to see strips in conjunction with information that is presented on the first page 100. For example, the physician may wish to see strips associated with high and low heart rate. The indication of where in the report strips can be found helps the physician navigate from the first page 100 to the strips, without requiring that the physician search through multiple pages of the report, and avoids or reduces the need for the relevant strips to actually be presented on the first page 100.

The representative arrhythmia summary section 110 includes information retained by the priority data filter regarding various types of arrhythmia. For example, the top section of the representative arrhythmia summary section 110 includes information about atrial fibrillation (AF). In particular, this section includes information about the fastest AF (i.e., AF associated with the highest rate) that occurred during the monitoring period. The date, time, and heart rate is shown for the fastest AF in both symptomatic and asymptomatic conditions. For the symptomatic fastest AF, the symptoms recorded by the patient are also shown. Detailed information is shown here for the fastest symptomatic and asymptomatic AF that occurred during the monitoring period. However, there may have been multiple occurrences of symptomatic and asymptomatic AF during the monitoring period. Accordingly, the representative arrhythmia summary section 110 also includes a total strip count describing how many strips with findings of symptomatic AF are in the report and how many strips with findings of asymptomatic AF are in the report. The representative arrhythmia section includes similar information for fastest supraventricular tachycardia (SVT), longest pause, slowest heart block, and fastest ventricular tachycardia (VT). The representative arrhythmia summary section 110 also includes an indication of on which page of the report strips begin to be presented. This indication is helpful for similar reasons as discussed above in relation to the indication in the HR summary section 108.

The AF summary section 112 includes information retained by the priority data filter about AF burden, analysis time, total time in AF, number of AF episodes, longest AF, highest heart rate during AF, lowest heart rate during AF, average heart rate during AF, highest heart rate not during AF, lowest heart rate not during AF, and average heart rate not during AF.

In the physician comments section 114, a physician reading the report can insert comments and sign his/her name. As discussed above, the priority information that a physician would need is retained by the priority data filter and included on the first page 100. Accordingly, the priority data filter and the report help the physician be more efficient and effective by providing the physician with the ability to analyze the priority data, provide comments, and sign, all while using just the first page 100 of the report.

The priority data filter retains priority information that a physician needs for interpreting collected data. This priority information is presented on the first page 100 of the report. This is helpful because the physician does not need to search through multiple pages of the report to find important information needed for interpreting the collected data. Also, the priority data filter does not retain graphs and strips for inclusion on the first page 100 of the report. This is helpful because graphs and strips occupy a large amount of space, and therefore including graphs and strips on the first page may not be the most efficient use of space on the first page. For example, while a strip may show information about one event, the space occupied by that strip can be used for showing other priority information retained by the priority data filter, such as information about multiple events. For example, rather than showing a strip about one event, it is possible to show on the first page 100 summary information about twelve events in the representative arrhythmia summary section 110.

Figure 7A:
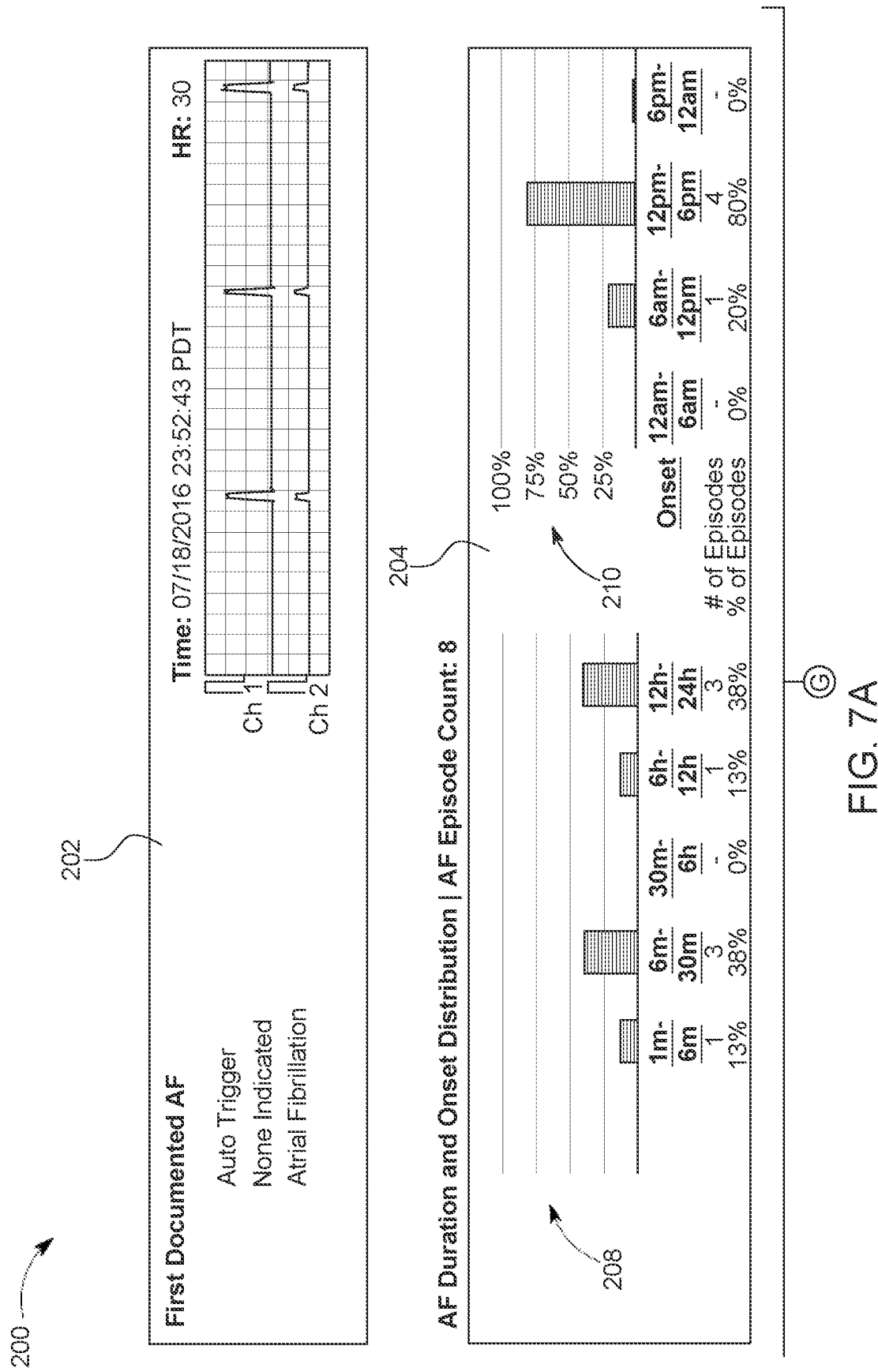
FIGS. 7A and 7B show an illustrative page 200 of an end of service summary report in accordance with some embodiments of the disclosure.
Figure 7B:
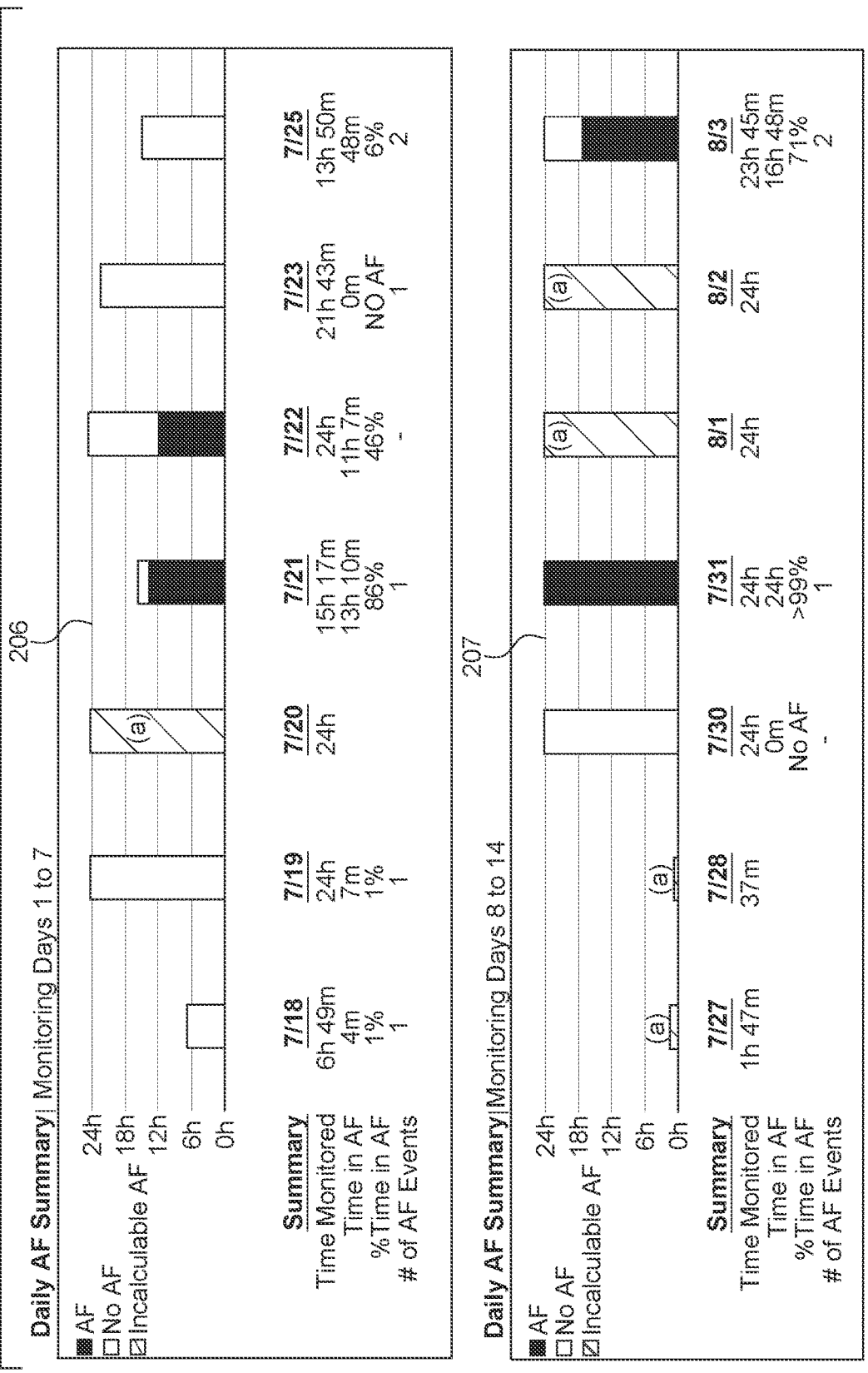

FIGS. 7A and 7B show a page 200 of an end of service summary report in accordance with some embodiments of the disclosure. The page 200 includes a first documented AF section 202, an AF duration and onset distribution section 204, and daily AF summary sections 206 and 207. The first documented AF section 202 show the date, time, heart rate, recorded symptoms (if any), recorded activities (if any), findings, and strip associated with the first occurrence of AF detected during the monitoring period. Information regarding the first occurrence of AF is important for a physician in analyzing data from an MCOT device. Accordingly, inclusion of information and a strip regarding the first occurrence of AF in its own section, near the beginning of the report, can be helpful in enabling the physician to efficiently and effectively analyze data from the MCOT device.

The AF duration and onset distribution section 204 shows histograms of AF data. A duration histogram 208 shows how many and what percentage of the total AF episodes occurred within a number of ranges of times. For example, the duration histogram 208 shows that 3 AF episodes, corresponding to 38% of the total AF episodes, were of a duration between 6 minutes and 30 minutes. An onset histogram 210 shows how many and what percentage of the total AF episodes occurred within a number of ranges of times of day. For example, the onset histogram 210 shows that 4 AF episodes, corresponding to 80% of the total AF episodes, had onsets between 12 pm and 6 pm. The AF duration and onset distribution section 204 also shows an indication of the total count of AF episodes during the monitoring period.

The daily AF summary sections 206 and 207 show bar graphs of AF data. In particular, for each of days 1-14 of the monitoring period, the daily AF summary sections 206 and 207 shows the total monitored time for the day, how much of the monitored time was spent in AF, and how much of the monitored time was spent not in AF. For example, in the daily AF summary section 207, the total monitored time for August 3 was 23 hours and 45 minutes, the total time spent in AF was 16 hours and 48 minutes, the percentage of the monitored time spent in AF was 71%, and the number of AF events was 2. Additionally, the height of the bar for August 3, when read against the vertical time axis, shows the total monitored time, the height of the blue section of the bar shows the total time spent in AF, and the height of the white section of the bar shows the total time not spent in AF. A legend indicates the meanings of the blue and white colors. The daily AF summary section 206 shows daily AF summary data for days 1-7 of the monitoring period and the daily AF summary section 207 shows daily AF summary date for days 8-14 of the monitoring period.

Figure 8A:
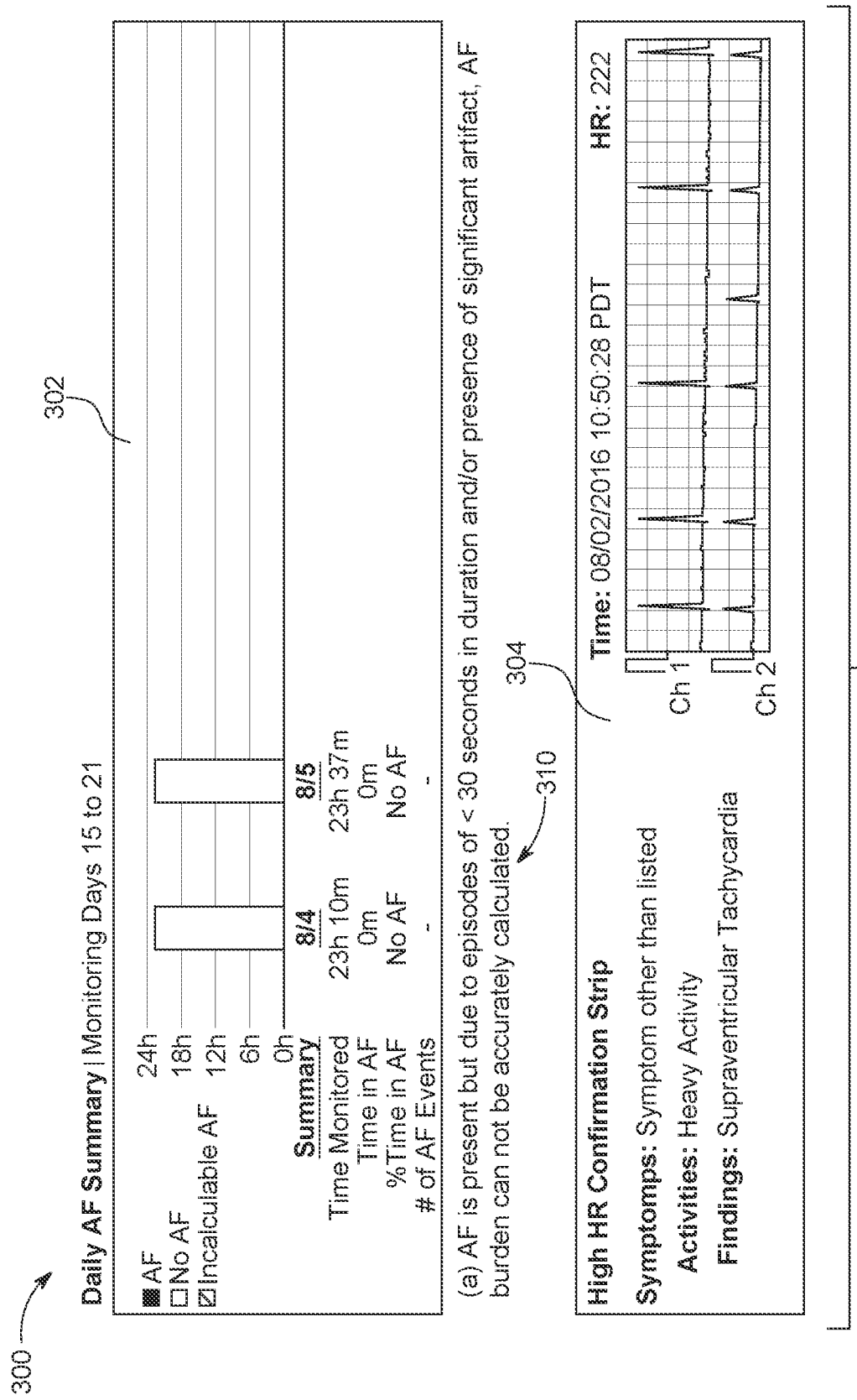
FIGS. 8A and 8B show an illustrative page 300 of an end of service summary report in accordance with some embodiments of the disclosure.
Figure 8B:
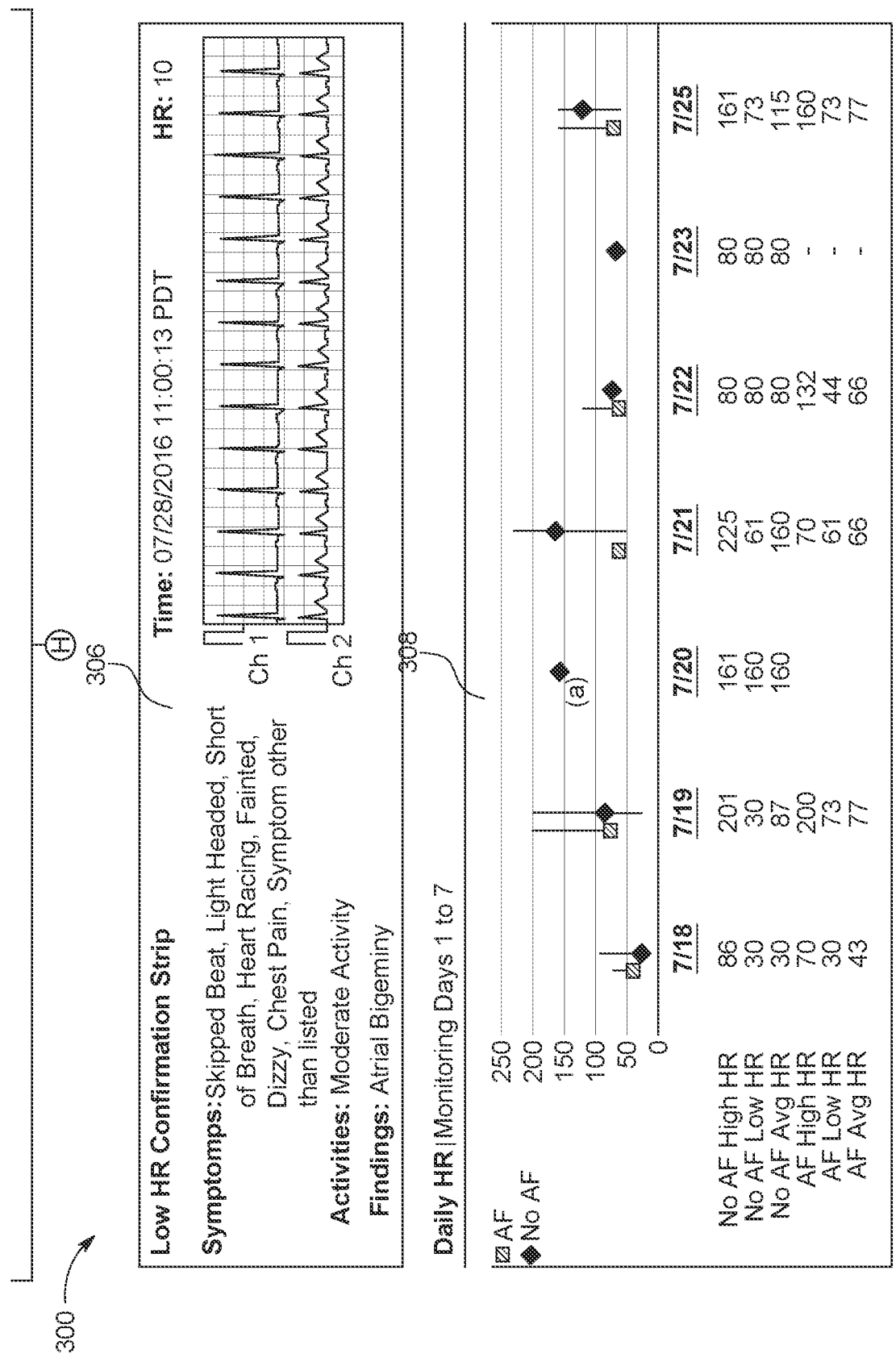

FIGS. 8A and 8B show a page 300 of an end of service summary report in accordance with some embodiments of the disclosure. The page 300 includes a daily AF summary section 302, a high HR confirmation strip section 304, a low HR confirmation strip section 306, and a daily HR section 308.

The daily AF summary section 302 is a continuation of the daily AF summary sections 206 and 207, showing daily AF summary data for days 15-21 of the monitoring period.

When page 200 and page 300 are adjacent to each other, the first documented AF section 202, the AF duration and onset distribution section 204, and the daily AF summary sections 206, 207, and 302 are adjacent to each other. Accordingly, information about AF summary can be found in one section organized around AF. This is helpful because the physician, when considering AF, will have the AF information in one section and will not have to search through multiple pages of the report to find information about AF. Furthermore, organizing information in the report by category means that the information is presented in a more sensible and understandable manner and may help the physician interpret the data efficiently and effectively as the physician reads through the report.

Certain bars in the daily AF summary sections 206 and 207 are filled with hatch lines. The legend indicates that hatch lines refer to incalculable AF. It may not be possible to calculate time spent in AF during a certain time period if, for example, artifacts occur in data from that time period. In addition to the hatch lines, a letter "(a)" on the bars with incalculable AF directs a physician reading the report to a disclaimer 310. The disclaimer 310 indicates that AF is present but due to episodes of <30 seconds in duration and/or presence of significant artifact, AF burden cannot be accurately calculated. Including the disclaimer 310 helps a physician avoid confusion about why AF may not have been calculated for a certain time period.

The high HR confirmation strip section 304 shows information about the time, date, heart rate value, recorded symptoms, recorded activities, and findings associated with the occurrence of the highest heart rate during the monitoring period. In some cases, algorithms for calculating the highest heart rate during the monitoring period may find that data associated with the occurrence of the highest heart rate contains artifacts. Accordingly, the algorithms may not have an acceptably high confidence that the highest heart value is accurate, rather than being due to the artifacts. In such situations, the patient report may not show this data. Instead, the patient report may show the highest heart rate associated with data that has an acceptably low number of artifacts, even if the other data that contains the artifacts indicates a higher heart rate. Accordingly, a physician reviewing the chart may be able to have confidence that the high heart rate information shown in the high HR confirmation strip section 304 is not corrupted by artifacts. The physician may be able to request, separately from the report, the other high heart rate information about which the algorithms did not have acceptably high confidence.

The low HR confirmation strip section 306 shows information about the time, date, heart rate value, recorded symptoms, recorded activities, and findings associated with the occurrence of the lowest heart rate during the monitoring period. In some cases, it is possible for a pause to corrupt calculation of lowest heart rate. For example, heart rate may be calculated by counting the number of beats during a given window of time, such as 20 seconds. If during that 20-second window, 10 beats occurred in the first 10 seconds, while a 10-second long pause occurred in the last 10 seconds, the heart rate may be calculated as 30 bpm. However, a more accurate interpretation of this data may be that a period of 60 bpm heart rate was followed by a 10-second pause. In other words, the occurrence of the pause may be a more important finding than the contribution of the pause to a low heart rate calculation. In such situations, the patient report may not include the pause event in calculations of lowest heart rate. Following the above example, the 10-second long pause would not be included in the calculation of heart rate. Accordingly, a physician reviewing the chart may be able to have confidence that the low heart rate information shown in the low HR confirmation strip section 306 is not corrupted by a pause. However, the pause, being a significant finding, would likely be represented in another portion of the report.

The daily HR section 308 shows a chart of HR data from days 1-7 of the monitoring period. In particular, the daily HR section 308 shows, for each day, the highest HR that occurred during a period of no AF, the lowest HR that occurred during a period of no AF, the average HR that occurred during periods of no AF, the highest HR that occurred during a period of AF, the lowest HR that occurred during a period of AF, and the average HR that occurred during periods of AF. For example, on July 19, the highest HR that occurred during a period of no AF was 201 bpm, the lowest HR that occurred during a period of no AF was 30 bpm, the average HR that occurred during periods of no AF was 87 bpm, the highest HR that occurred during a period of AF was 200 bpm, the lowest HR that occurred during a period of AF was 73 bpm, and the average HR that occurred during periods of AF was 77 bpm. In addition, for each day, the position of a yellow square, when read against the vertical axis, represents the average HR during periods of AF, and the position of a blue diamond represents the average HR during periods of no AF. Furthermore, the tip of a yellow line extending upwards represents the highest HR that occurred during a period of AF, the tip of a yellow line extending downwards represents the lowest HR that occurred during a period of AF, the tip of a blue line extending upwards represents the highest HR that occurred during a period of no AF, the tip of a blue line extending downwards represents the lowest HR that occurred during a period of no AF. A legend indicates the meaning of the shapes and colors of the chart. In some cases, if the lowest and/or highest HR value is close to the average HR value, lines indicating the lowest and/or highest HR values may not be visible beyond the shape representing the average HR value. For example, on July 19, the yellow square represents the average HR value of 77 during periods of AF, the tip of the yellow line extending upwards represents the highest HR value of 200 that occurred during periods of AF, but no yellow line extending downwards is visible because the lowest HR value of 73 that occurred during periods of AF is close to the average HR value of 77 during periods of AF.

Figure 9A:
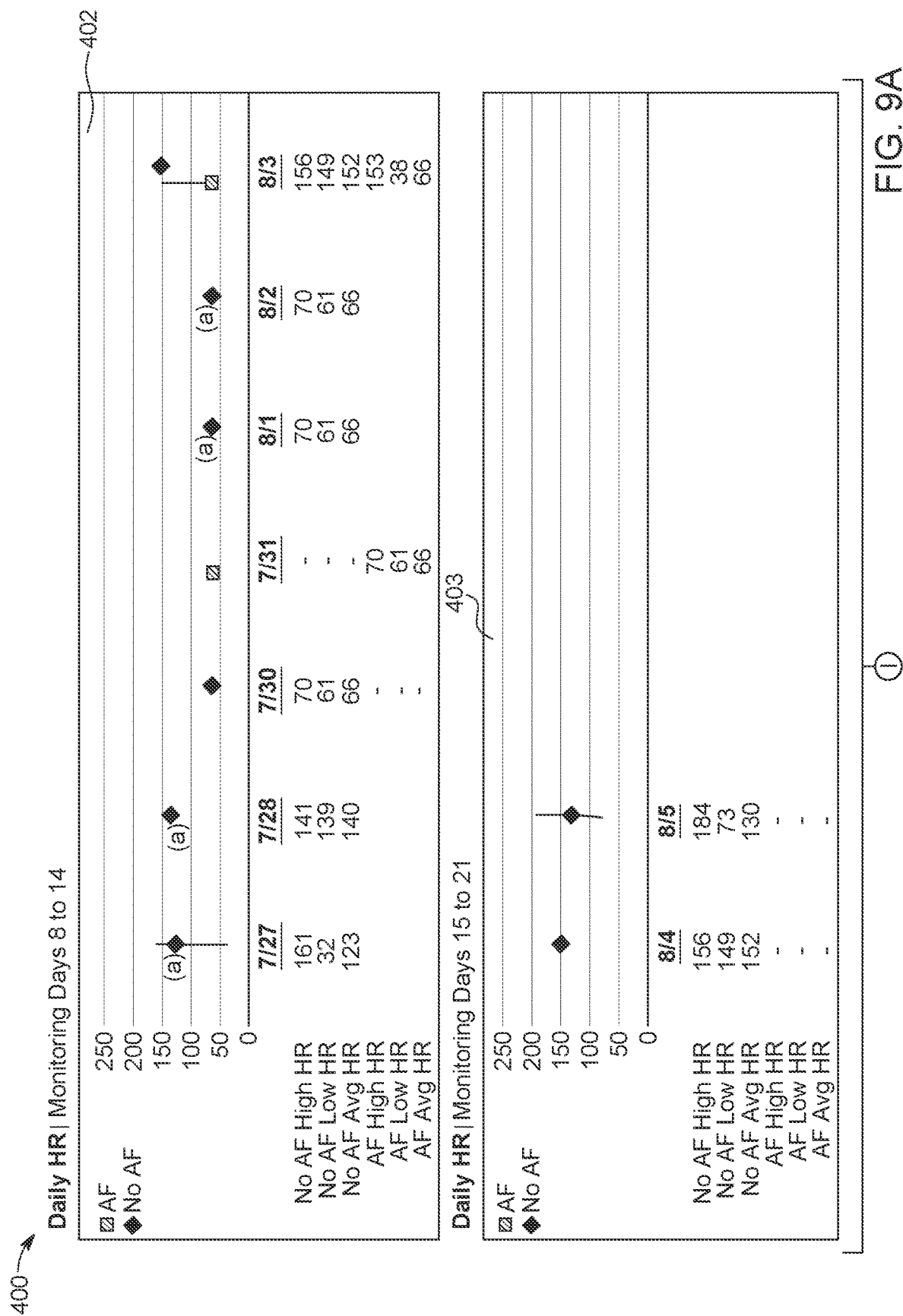

FIGS. 9A and 9B show a page 400 of an end of service summary report in accordance with some embodiments of the disclosure. The page 400 includes daily HR sections 402 and 403 and emergent/urgent summary section 404. The daily HR sections 402 and 403 are continuations of the daily HR section 308, showing daily AF summary data for days 8-14 and 15-21, respectively, of the monitoring period. For certain days in the daily HR sections 308, 402, and 403, information regarding HR during AF is not present. For similar reasons as discussed above, it may not be possible to calculate time spent in AF if, for example, artifacts occur in data. A letter "(a)" directs a physician reading the report to a disclaimer 406 similar to disclaimer 310. Including the disclaimer 406 helps the physician avoid confusion about why AF may not have been calculated.

When page 300 and page 400 are adjacent to each other, the high HR confirmation strip section 304, the low HR confirmation strip section 306, and the daily HR sections 308, 402, and 403 are adjacent to each other. Accordingly, information about HR summary can be found in one section organized around HR. This is helpful because the physician, when considering HR, will have HR information in one section and will not have to search through multiple pages of the report to find information about HR. Furthermore, organizing information in the report by category means that the information is presented in a more sensible and understandable manner and may help the physician interpret the data efficiently and effectively as the physician reads through the report.

The emergent/urgent summary section 404 lists times, dates, recorded symptoms, findings, and heart rates for emergent/urgent events. The time and date for each emergent/urgent event can be used to find the corresponding strip in a strip section later in the report.

FIGS. 10A and 10B show a page 500 of an end of service summary report in accordance with some embodiments of the disclosure. The page 500 includes a continuation of the emergent/urgent summary section 404.

FIGS. 11A and 11B show a page 600 of an end of service summary report in accordance with some embodiments of the disclosure. The page 600 includes a continuation of the emergent/urgent summary section 404 and a symptomatic events summary section 602. The symptomatic events summary section 602 lists times, dates, recorded symptoms, findings, and heart rates for events associated with patient recordings of symptoms. The time and date for each symptomatic event can be used to find the corresponding strip in a strip section later in the report.

FIGS. 12A and 12B show a page 700 of an end of service summary report in accordance with some embodiments of the disclosure. The page 700 includes a continuation of the symptomatic events summary section 602.

FIGS. 13A and 13B show a page 800 of an end of service summary report in accordance with some embodiments of the disclosure. The page 800 includes a continuation of the symptomatic events summary section 602 and a strip summary section 802. The strip summary section 802 includes, for each collected event, the time, date, finding, recorded symptom, recorded activity, heart rate, and strip. Events are listed in chronological order in the strip summary section 802. Accordingly, if an event with a particular time and date is identified elsewhere in the report (e.g., the HR summary section 108, the representative arrhythmia summary section 110, the first documented AF section 202, the high HR confirmation strip section 304, the low HR confirmation strip section 306, the emergent/urgent summary section 404, and the symptomatic events summary section 602), a physician reviewing the report can easily find the corresponding strip in the strip summary section 802. The strip summary section 802 is present towards the end of the report. Not including many strips at the beginning of the report is beneficial because strips occupy a large amount of space, and therefore including strips at the beginning of the report, which may be the focus of the physician's attention, may not be the most efficient use of space on the first page. For example, while a strip may show detailed information about one event, the space occupied by that strip could be used for showing information about multiple events.

FIGS. 14-30 show further illustrative pages of the end of service summary report in accordance with some embodiments of the disclosure that include continuations of the strip summary section 802.

Certain events may have two associated findings. For example, a single event may have findings of advanced heart block and 8 second pause. In such a case, the same event may be shown as two strips in the strip summary section 802. As seen in FIG. 19, a single event on Jul. 20, 2016, at 4:59:11 PDT corresponds to both advanced heart block at 8 second pause. Accordingly, it may be important to ensure that findings are counted in terms of strips, and not in terms of events. Otherwise, the above example would be counted as just one event even though there are two corresponding strips, which could be confusing for a physician reviewing the report. As seen in the representative arrhythmia summary section 110, for example, total strip counts, rather than total event counts, are shown.

The foregoing is merely illustrative of the principles of the disclosure, and the data filter and report can be practiced by other than the described embodiments, which are presented for purposes of illustration and not of limitation. It is to be understood that while various sections are described as occurring on certain pages of a report, the sections can also be presented on other pages of the report, and various sections can be presented in different orders than the order described above.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

We claim:

1. A method for filtering and indexing ECG data, the method comprising:
   receiving ECG data of a patient and indications of patient-recorded symptoms from a mobile cardiac telemetry device;
   identifying atrial fibrillation events in the received ECG data;
   for each identified atrial fibrillation event, filtering the received ECG data to determine whether the identified atrial fibrillation event coincided temporally with at least one patient-recorded symptom, and labeling each such coinciding identified atrial fibrillation events as an asymptomatic AF strip and each non-coinciding identified atrial fibrillation events as an asymptomatic AF strip;
   generating an ECG report based on the filtered ECG data, the report comprising a sequence of a plurality of pages;
   presenting, on a first page in the sequence of the plurality of pages:
      representative arrhythmia summary information including a count of ECG strips containing each of a plurality of types of cardiac arrhythmia, and
      atrial fibrillation summary information including an indication of atrial fibrillation burden during the monitoring period;
      a count of symptomatic AF strips; and
      a count of asymptomatic AF strips;
   wherein at least one page of the plurality of pages includes an ECG strip, but the first page in the sequence does not include an ECG strip;
   determining a strip address by determining an earliest page of the sequence of the plurality of pages that includes an ECG strip;
   determining an AF summary address by determining an earliest page of the sequence of the plurality of pages that includes the atrial fibrillation summary information; and
   presenting, on the first page in the sequence, an address index comprising:
      a strip pointer comprising the strip address and, adjacent thereto, a signifier of an ECG strip; and
      an AF summary pointer comprising the AF summary address and,
      adjacent thereto, a signifier of atrial fibrillation.

2. The method of claim 1, wherein the first page does not include a graph of ECG data.

3. The method of claim 2, further comprising calculating the lower heart rate of the patient, wherein a portion of ECG data is excluded from calculation of the lowest heart rate if the portion includes a pause event.

4. The method of claim 2, further comprising:
receiving an artifact threshold, and
calculating the highest heart rate of the patient, wherein a portion of ECG data is excluded from calculation of the highest heart rate if the portion includes an amount of artifact that exceeds the artifact threshold.

5. The method of claim 2, wherein the representative arrhythmia summary information includes the date, time, and heart rate corresponding to:
a fastest atrial fibrillation,
a fastest supraventricular tachycardia,
a longest pause,
a slowest heart block, and
a fastest ventricular tachycardia.

6. The method of claim 5, further comprising counting of ECG strips pertaining to arrhythmia events included in the representative arrhythmia summary, wherein the representative arrhythmia summary information includes a count of ECG strips containing atrial fibrillation, a count of ECG strips containing heart block, a count of ECG strips containing pause, a count of ECG strips containing supraventricular tachycardia, and a count of ECG strips containing ventricular tachycardia.

7. The method of claim 6, wherein symptomatic arrhythmia events are counted separately from asymptomatic arrhythmia events.

8. The method of claim 7, wherein the representative arrhythmia summary information includes, for symptomatic arrhythmia events, an indication of symptoms associated with the symptomatic arrhythmia events as recorded by the patient.

9. The method of claim 8, further comprising presenting event summary information on the first page, wherein the event summary information includes an indication of an earliest page on which ECG strips are presented.

10. The method of claim 9, wherein the event summary information includes an indication of a total number of ECG strips presented in the report.

11. The method of claim 10, further comprising monitoring summary information including an indication of a total duration of a monitoring period, which contains a number of days for which a monitoring device was prescribed to the patient, a number of dates in which monitoring occurred, a baseline date, and an end date.

12. The method of claim 1, wherein the atrial fibrillation summary information includes total time in atrial fibrillation, number of atrial fibrillation episodes, longest atrial fibrillation, highest heart rate during atrial fibrillation, lowest heat rate during atrial fibrillation, average heart date during atrial fibrillation, highest heart rate not during atrial fibrillation, lowest heart rate not during atrial fibrillation, and average heart rate not during atrial fibrillation.

13. The method of claim 1, further comprising presenting, on a second page, a histogram of atrial fibrillation duration, a histogram of atrial fibrillation onset, and an indication of daily atrial fibrillation burden for each of a plurality of days in the monitoring period.

14. The method of claim 13, further comprising presenting, on the second page, total time in atrial fibrillation, number of atrial fibrillation episodes, longest atrial fibrillation, highest heart rate during atrial fibrillation, lowest heart rate during atrial fibrillation, average heart rate during atrial fibrillation, highest heart rate not during atrial fibrillation, lowest heart rate not during atrial fibrillation, and average heart ate not during atrial fibrillation.

15. A system for filtering and indexing ECG data, the system comprising:

a processor; and
computer-readable memory storing instructions which, when executed by the processor, cause the processor to perform operations comprising:
receiving ECG data of a patient and indications of patient-recorded symptoms from a mobile cardiac telemetry device;
identifying atrial fibrillation events in the received ECG data;
for each identified atrial fibrillation event, filtering the received ECG data to determine whether the identified atrial fibrillation event coincided temporally with at least one patient-recorded symptom, and labeling each such coinciding identified atrial fibrillation events as an asymptomatic AF strip and each non-coinciding identified atrial fibrillation events as an asymptomatic AF strip;
generating an ECG report based on the filtered ECG data, the report comprising a sequence of a plurality of pages;
presenting, on a first page in the sequence of the plurality of pages:
representative arrhythmia summary information including a count of ECG strips containing each of a plurality of types of cardiac arrhythmia, and
atrial fibrillation summary information including an indication of atrial fibrillation burden during the monitoring period;
a count of symptomatic AF strips; and
a count of asymptomatic AF strips;
wherein at least one page of the plurality of pages includes an ECG strip, but the first page in the sequence does not include an ECG strip;
determining a strip address by determining an earliest page of the sequence of the plurality of pages that includes an ECG strip;
determining an AF summary address by determining an earliest page of the sequence of the plurality of pages that includes the atrial fibrillation summary information; and
presenting, on the first page in the sequence, an address index comprising:
a strip pointer comprising the strip address and, adjacent thereto, a signifier of an ECG strip; and
an AF summary pointer comprising the AF summary address and,
adjacent thereto, a signifier of atrial fibrillation.

16. The system of claim 15, wherein the first page does not include a graph of ECG data.

17. The system of claim 16, wherein the operations further comprise calculating the lower heart rate of the patient, wherein a portion of ECG data is excluded from calculation of the lowest heart rate if the portion includes a pause event.

18. The system of claim 16, wherein the operations further comprise:
receiving an artifact threshold, and
calculating the highest heart rate of the patient, wherein a portion of ECG data is excluded from calculation of the highest heart rate if the portion includes an amount of artifact that exceeds the artifact threshold.

19. The system of claim 16, wherein the representative arrhythmia summary information includes the date, time, and heart rate corresponding to:
a fastest atrial fibrillation,
a fastest supraventricular tachycardia,
a longest pause, a slowest heart block, and a fastest ventricular tachycardia.

20. The method of claim 19, further comprising counting of ECG strips pertaining to arrhythmia events included in the representative arrhythmia summary, wherein the representative arrhythmia summary information includes a count of ECG strips containing atrial fibrillation, a count of ECG strips containing heart block, a count of ECG strips containing pause, a count of ECG strips containing supraventricular tachycardia, and a count of ECG strips containing ventricular tachycardia.

\* \* \* \* \*